(12) United States Patent
Kim et al.

(10) Patent No.: US 9,963,708 B2
(45) Date of Patent: May 8, 2018

(54) RECOMBINANT VECTOR FOR FOREIGN GENE EXPRESSION WITHOUT BIOLOGICAL CIRCUIT INTERFERENCE OF HOST CELL AND USES THEREOF

(71) Applicant: INDUSTRY FOUNDATION OF CHONNAM NATIONAL UNIVERSITY, Gwangju (KR)

(72) Inventors: Geun Joong Kim, Gwangju (KR); Eun Bin Lee, Gwangju (KR); Sung Hwan You, Gwangju (KR)

(73) Assignee: INDUSTRY FOUNDATION OF CHONNAM NATIONAL UNIVERSITY, Gwangju (KR)

( * ) Notice: Subject to any disclaimer, the term of this patent is extended or adjusted under 35 U.S.C. 154(b) by 0 days. days.

(21) Appl. No.: 14/410,063

(22) PCT Filed: Jul. 1, 2014

(86) PCT No.: PCT/KR2014/005807
§ 371 (c)(1),
(2) Date: Dec. 20, 2014

(87) PCT Pub. No.: WO2015/147379
PCT Pub. Date: Oct. 1, 2015

(65) Prior Publication Data
US 2017/0002364 A1    Jan. 5, 2017

(30) Foreign Application Priority Data
Mar. 26, 2014 (KR) .................. 10-2014-0035119

(51) Int. Cl.
| C12N 15/00 | (2006.01) |
|---|---|
| C12N 5/00 | (2006.01) |
| C12P 21/06 | (2006.01) |
| C12N 15/70 | (2006.01) |
| C12N 15/10 | (2006.01) |
| C12P 21/00 | (2006.01) |

(52) U.S. Cl.
CPC ......... C12N 15/70 (2013.01); C12N 15/1055 (2013.01); C12P 21/00 (2013.01)

(58) Field of Classification Search
None
See application file for complete search history.

(56) References Cited

U.S. PATENT DOCUMENTS 5,652,131 A * 7/1997 Beavo ................ C12N 9/16
435/196

FOREIGN PATENT DOCUMENTS

| KR | 10-0958095 B1 | 5/2010 |
|---|---|---|
| KR | 10-2010-0075884 A | 7/2010 |

OTHER PUBLICATIONS

Marden et al in "Cyclic GMP Controls Rhodospirillum Centenum Cyst Development" (Molecular Microbiology, Jan. 9, 2011, vol. 79, No. 3, pp. 600-615).*
Pilz et al in "Regulation of Gene Expression by Cyclic GMP" (Circulation Research, Nov. 28, 2003, vol. 93, No. 11, pp. 1034-1046).*
Berleman & Bauer in "A che-like signal transduction cascade involved in controlling flagella biosynthesis in Rhodospirillum centenum" (Molecular Microbiology vol. 55, No. 5, 2005, pp. 1390-1402).*
Score result for SEQ ID No. 1 Lu et al in "Metabolic flexibility revealed in the genome of the cyst-forming alpha-1 proteobacterium Rhodospirillum centenum" (BMC Genomics 2010, vol. 11, 325).*
Score result Berleman and Bauer SEQ ID No. 7.*
Score result Berleman and Bauer SEQ ID No. 6.*
Score result for SEQ ID No. 3 Lu et al in "Metabolic flexibility revealed in the genome of the cyst-forming alpha-1 proteobacterium Rhodospirillum centenum" (BMC Genomics 2010, vol. 11, 325).*
Hanahan, D., Studies on Transformation of *Escherichia coli* with Plasmids, J. Mol. Biol., 166:557-580 (1983).

* cited by examiner

*Primary Examiner* — Catherine S Hibbert
(74) *Attorney, Agent, or Firm* — The PL Law Group, PLLC

(57) ABSTRACT

A recombinant vector enables independent expression of a foreign gene without interfering with a biological circuit of a host cell. A gene encoding a guanylyl cyclase, a gene encoding cGMP receptor protein, and a regulatory nucleotide sequence to which cGMP receptor protein binds, which are derived from a microorganism, are recombined in at least one plasmid. Using the recombinant vector, a foreign gene may be independently expressed without interfering with a biological circuit of a host cell.

15 Claims, 18 Drawing Sheets

Schematic diagram of cGMP-dependent orthogonal signal transduction system

Completed signal transduction system construct

Completed signal transduction system construct

Control construct

A) 0.1mM IPTG induction in case of OD600 = 0.5

B) 0.1mM IPTG induction in case of OD600 = 0.7

Completed signal amplification system construct

RECOMBINANT VECTOR FOR FOREIGN GENE EXPRESSION WITHOUT BIOLOGICAL CIRCUIT INTERFERENCE OF HOST CELL AND USES THEREOF

CROSS REFERENCE TO RELATED APPLICATIONS AND CLAIM OF PRIORITY

This patent application is a National Stage entry from International Application No. PCT/KR2014/005807, filed Jul. 1, 2014, which claims priority to Korean Patent Application No. 10-2014-0035119, filed Mar. 26, 2014, entire contents of which are incorporated herein by reference.

BACKGROUND

Technical Field

The present invention relates to a recombinant vector for expressing a foreign gene without interfering a biological circuit of a host cell and a use thereof. More specifically, it relates to a recombinant vector for expressing independently a foreign gene without interfering a biological circuit of a host cell, characterized in that a gene encoding guanylyl cyclase, a gene encoding cGMP receptor protein, and a regulatory nucleotide sequence to which a cGMP receptor protein binds, which are derived from a microorganism, are recombined in at least one plasmid, a method for independent expression of a foreign gene without interfering a biological circuit of a host cell by transforming a host cell with a recombinant vector in which a foreign gene is operably linked to the aforementioned recombinant vector, a host cell transformed with the aforementioned recombinant vector, and a composition and a kit comprising, as an effective component, the aforementioned recombinant vector for enhancing expression of a foreign gene without interfering a biological circuit of a host cell.

Background Art

Technologies for expressing and producing a protein based on genetic recombination are fundamental tools in bioscience research and biological industries. In particular, due to the easiness of gene manipulation and host culture and excellence of protein expression, a method for producing a protein by using microorganisms or yeast is employed for a process for producing various recombinant proteins for research and also industrial application. Such technologies can be used for production of highly valuable products like bio-fuel, food ingredients, and pharmaceutical agents when they are applied to metabolic engineering for producing recombinant proteins based on incorporation of a foreign gene or for inducing over-expression of useful products based on manipulation of a metabolic circuit of a host.

As it has been already known, when a foreign DNA is introduced to and expressed in a host cell, the metabolic physiology intrinsic to the host may be changed or disturbed as the normal cell function is affected by it. Such phenomenon is referred to as metabolic burden that is harmful or stressful to a host by a foreign DNA, and it includes various side effects like triggering synthesis of stress-responsive proteins and inhibited cell function as caused by over-expression of a protein or activity of a recombinant protein. In particular, since a gene expression system intrinsic to a host (e.g., transcriptional and translational elements) needs to be shared during the expression process of a foreign recombinant gene, when over-expression of a foreign recombinant gene is induced, transcriptional/translational elements and resources that are needed for the host are depleted, and thus growth retardation by disturbed physiology is caused. Such phenomenon leads to increased stress, especially when a recombinant gene expression was induced explosively within a short time, and the increased stress induces simultaneous expression of a chaperon or a protease for lowering the physiological burden on the host, and thus degradation of a protein and physicochemical change of a cell membrane are caused. In the end, it causes decreased yield of a target product. When a multi-step enzyme reaction is required for producing a specific product, in particular, the genes relating thereto need to be expressed in multiple- or operon-mode in order to construct artificially a production pathway. Accordingly, various genes need to be expressed simultaneously in a large amount via a gene expression module or a genetic circuit consisting of one or more types of inducible expression system (IPTG-LacI, L-arabinose-AraC, and anhydrotetracycline-TetR). As a result, a more severe physiological burden will be inflicted to the host.

As a way of avoiding problems like delayed growth or contamination (i.e., products of unexpected metabolism) caused by disturbance or stress in cell physiology by lowering mutual interference with expression of a foreign gene (i.e., interference based on sharing of machinery for translation and transcription within a host), a cell free reaction method in which main components required for gene expression are extracted from a cell, mixed with a target gene, and used for ex vivo protein synthesis or reaction is considerable. Because this method allows efficient reaction/synthesis within a short time and does not require cell culture, it is advantageous in terms of minimizing the processes of separation and purification. However, it also has a problem of being expensive and requiring careful control of experimental conditions. Further, unlike a system in which cells are used as an expression system, it is impossible to have regeneration of cellular components, such as cofactors and also de-novo synthesis of macromolecule, such as RNA and ribosome and thus there is a clear limitation in productivity. Thus, basically it is more advantageous to produce a protein or a metabolic product by designing a suitable regulatory mechanism of a living cell which is capable of division. As the most suitable method satisfying such purpose, there is a method of using an orthogonally functional factor such that a selective reaction or gene expression is obtained functionally separately from an innate gene expression system of a host by introducing an expression system that can be independently regulated. For example, when a set including an orthogonal mRNA (O-mRNA) having a Shine-Dalgarno sequence which has been modified so as not to be recognized by an innate ribosome, an orthogonal ribosome (O-ribosome) for recognizing this O-mRNA, and an orthogonal aminoacyl-tRNA synthetase (O-aminoacyl tRNA synthetase) is used, a system for independent protein production without using a translation apparatus of a host can be achieved. From the viewpoint of physiology of a host, O-mRNA and O-ribosome are a non-essential element and they enable a route for synthesizing a protein without using innate translation network of a host. However, there is also a problem that translational delay may occur in terms of gene expression and, due to relatively low amount of an orthogonal factor in living cells, the protein expression level is lower than a case in which an innate system is used. Meanwhile, a method of using T7 RNA polymerase is also known as an orthogonal system for transcriptional process other than the aforementioned translational process. According to this process, a polymerase derived from a phage and a corresponding promoter are used to avoid competition with transcriptional tools that are intrinsic to a host (i.e., RNA polymerase binding to promoter). However, the problem to be solved in this orthogonal transcriptional system is that complete independency is not guaranteed. That is because the selectivity of a conserved sequence of prokaryotic promoter or a polymerase binding to the sequence is relatively low as it is generally known. It has been found that the T7 RNA polymerase can bind at certain level also to a promoter intrinsic to a host and the T7 promoter also can be recognized by innate E. coli RNA polymerase. As such, an interaction mediated by transcriptional factors of a host is possible, and therefore a transcript is detected at or above certain level even without an inducing agent. In spite of those disadvantages, expressing a target gene by using an operation factor independent from a host expression system is still a promising expression logic which draws attention. However, although an applicable orthogonal system exists partially at transcription and translation level, systematic construction of an orthogonal system has not been established yet. In this regard, the problem resides in that typical logic for transcriptional regulation used for in vivo expression of an orthogonal ribosome or RNA polymerase is dependent on a method which may disturb the metabolism and physiology of a host, i.e., IPTG/lac repressors, arabinose/AraC, or the like that are commonly used in a related art. That is because, the main component responsible for transcription and translation is orthogonal but the logic for controlling/regulating it is not orthogonal, and thus IPTG (or lactose) and arabinose introduced as a signal for inducing expression of orthogonal factor may be involved with or interfere with the expression or regulation of other genes that are related to a sugar metabolism in living cells. From this point of view, recently reported studies in which a kinase cascade signal transduction system of eukaryotic cells is introduced to and operated in prokaryotic cells (*E. coli*) can be an alternative way of solving the present problems based on good expression regulation logic of an orthogonal system. However, for general application, there are still unsatisfying results from characteristic evaluation, and thus more generally applicable expression regulation logic of an orthogonal factor is required.

Under the circumstances, the inventors of the present invention succeeded in producing a signal separate from a host (i.e., orthogonalization without mutual interference) by obtaining a complete set of constitutional components that are related to transcriptional signal transduction (induction) from a microorganism of a species which is different from *Escherichia coli* and by operating the set in *E. coli*, and also confirmed simultaneous multi-gene expression of which expression is induced by signal amplification using the produced signal (i.e., amplification of a small amount of signal) and receiving simultaneously those multiple signals (i.e., mimicking global regulation in which multi-gene expression is regulated by a single signal). The present invention is completed accordingly.

Meanwhile, a "method for the mass expression of an antimicrobial peptide by using a translational coupling system" is disclosed in Korean Patent Registration No. 0958095, and a "method to increase transgene expression from bacterial-based delivery systems by co-expressing suppressors of eukaryotic type I interferon response" is disclosed in Korean Patent Application Publication No. 2010-0075884. However, a recombinant vector for expressing a foreign gene without interfering with a biological circuit of a host cell and a use thereof have not been described at all.

SUMMARY

The present invention is devised under the circumstances described above, and inventors of the present invention constructed a recombinant vector by using a guanylyl cyclase, cGMP receptor protein, and a regulatory nucleotide sequence to which cGMP receptor protein binds, which are separated from *Rhodospirillum centenum*, and inserted a foreign gene to the recombinant vector followed by transformation of *E. coli* cells. Further, by confirming that the expression of the foreign gene is induced with no influence on cell growth or a stress-responsible activity when compared to a control *E. coli* group which has been transformed with an empty vector, they completed the present invention.

In order to solve the problems described above, the present invention provides a recombinant vector enabling independent expression of a foreign gene without interfering with a biological circuit of a host cell, characterized in that a gene encoding a guanylyl cyclase, a gene encoding cGMP receptor protein, and a regulatory nucleotide sequence to which cGMP receptor protein binds, which are derived from a microorganism, are recombined in at least one plasmid.

The present also provides a recombinant vector enabling independent expression of a foreign gene without interfering with a biological circuit of a host cell, characterized in that a gene encoding cGMP receptor protein and a regulatory nucleotide sequence to which cGMP receptor protein binds, which are derived from a microorganism, are recombined in at least one plasmid.

The present also provides a method for independent expression of a foreign gene without interfering with a biological circuit of a host cell by transforming a host cell with a recombinant vector having a foreign gene inserted to the aforementioned recombinant vector.

The present also provides a composition or a kit for enhancing expression of a foreign gene without interfering with a biological circuit of a host cell comprising the aforementioned recombinant vector as an effective component.

The present also provides a method for determining an interaction between a bait and a prey, wherein the method includes detecting an interaction between a bait and a prey which have been expressed in *E. coli* after recombination of at least one of a bait or a prey with each of the catalytic domain and ATP hydrolyzing domain of guanylyl cyclase protein derived from a microorganism.

Due to the characteristic of not interfering with an expression signal intrinsic to a host cell, the recombinant vector of the present invention can alleviate a physiological burden on a host and also, by amplifying gene transcription activating signal using as a mediating factor a second messenger involved with intracellular signal transduction, can induce efficiently gene expression even with a small amount of initial signal. Based on such characteristics, it is unnecessary to have a large amount of chemically synthesized expensive inducing agents for gene expression. Thus, a large amount of the target product can be produced in an economically favorable manner and it is also suitable for a test with a living cell or body to which a large amount of a chemical inducing agent cannot be injected (i.e., drug delivery or gene therapy in which large amount injection of an expression signal is required due to long distance to the target cells or organs) or for large scale production of a pharmaceutical protein or an industrial enzyme in a fermenting apparatus or a culture bath. Further, as it can induce simultaneous expression of many genes, it is applicable to various fields of metabolic engineering and industrially useful application thereof is expected.

DETAILED DESCRIPTION

Figure 1:
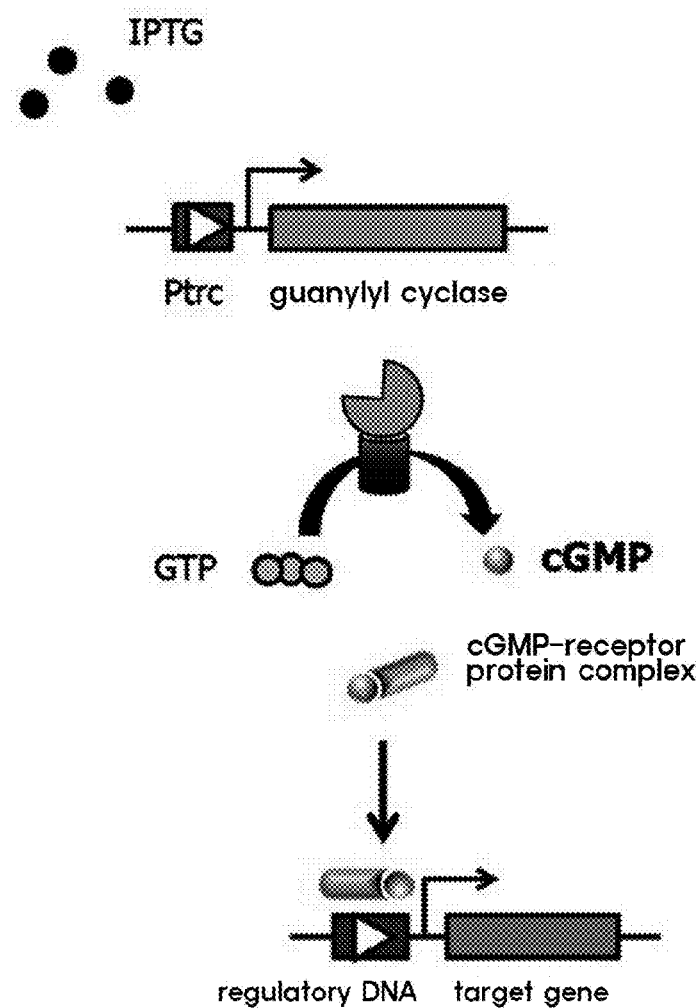
FIG. 1 is a schematic diagram explaining the operational principle of cGMP-dependent orthogonal signal transduction system of the present invention for inducing gene expression. In the diagram, a mechanism for inducing transcription by metabolites that are not generally used in common microorganisms, production of cGMP and a receptor for receiving the cGMP, and a cGMP-receptor complex are shown.

In order to achieve the purpose of the present invention, the present invention provides a recombinant vector enabling independent expression of a foreign gene without interfering with a biological circuit of a host cell, characterized in that a gene encoding a guanylyl cyclase, a gene encoding cGMP receptor protein, and a regulatory nucleotide sequence to which cGMP receptor protein binds, which are derived from a microorganism, are recombined in at least one plasmid.

The present also provides a recombinant vector enabling independent expression of a foreign gene without interfering with a biological circuit of a host cell, characterized in that a gene encoding cGMP receptor protein and a regulatory nucleotide sequence to which cGMP receptor protein binds, which are derived from a microorganism, are recombined in at least one plasmid.

According to the recombinant vector of one embodiment of the present invention, a gene encoding a guanylyl cyclase, a gene encoding cGMP receptor protein, and a regulatory nucleotide sequence to which cGMP receptor protein binds, which are derived from a microorganism, may be recombined in at least one plasmid. For example, it is possible that those three genes are recombined in separate plasmids, a gene encoding a guanylyl cyclase and a gene encoding cGMP receptor protein, which are derived from a microorganism, are recombined in one plasmid while a regulatory nucleotide sequence is inserted to other plasmid, or those three genes are inserted to one plasmid, and it is not specifically limited thereto.

Further, according to the recombinant vector of one embodiment of the present invention, cGMP may be artificially added instead of a gene encoding a guanylyl cyclase derived from a microorganism. In such case, the guanylyl cyclase is unnecessary, and thus it is possible that a gene encoding cGMP receptor protein and a regulatory nucleotide sequence, which are derived from a microorganism, are recombined in at least one plasmid.

According to the recombinant vector of one embodiment of the present invention, the microorganism may be *Rhodospirillum centenum*, but not limited thereto.

Guanylyl cyclase is an enzyme which produces 3',5'-cGMP (cyclic guanosine monophosphate) or 2',5'-cGMP by using GTP (guanosine triphosphate) as a substrate, and in *Rhodospirillum centenum* strain, it is known as class III nucleotidyl cyclase.

The gene of the present invention which encodes guanylyl cyclase may also include the nucleotide sequence that is represented by SEQ ID NO: 1. Further, the homologs of the aforementioned nucleotide sequence are also within the scope of the present invention. Specifically, the aforementioned gene may contain a nucleotide sequence with at least 70%, preferably at least 80%, more preferably at least 90%, and most preferably at least 95% sequence homology with the nucleotide sequence of SEQ ID NO: 1. The "sequence homology %" for a certain polynucleotide is determined by comparing two nucleotide sequences that are optimally arranged with a region to be compared. In this regard, a part of the polynucleotide sequence in a region to be compared may comprise an addition or a deletion (i.e., a gap) compared to a reference sequence (without any addition or deletion) relative to the optimized arrangement of the two sequences.

The "cGMP receptor protein" has a function of inducing transcription in accordance with binding to cGMP, and the gene encoding cGMP receptor protein as described herein may contain the nucleotide sequence that is represented by SEQ ID NO: 3. Further, the homologs of the aforementioned nucleotides are also within the scope of the present invention, and the details are as described above.

According to the recombinant vector of one embodiment of the present invention, the regulatory nucleotide sequence can be a nucleotide sequence derived from cyd2 (hybrid histidine kinase), pyrC' (dihydroorotase-like protein), cheY$_3$ (chemotaxis-like protein), or cstS1 (sensor-kinase-response regulator hybrid), but not limited thereto. With regard to the regulatory nucleotide sequence derived from cyd2, pyrC', cheY$_3$, or cstS1, the nucleotide sequences each represented by SEQ ID NO: 4, 5, 6 or 7 and homologs of those nucleotide sequences are within the scope of the present invention, and the details are as described above.

The present invention also provides a recombinant vector having a foreign gene inserted at downstream of the regulatory nucleotide sequence of the aforementioned recombinant vector.

The term "recombinant" indicates a cell which replicates a heterogeneous nucleotide or expresses said nucleotide, a peptide, a heterogeneous peptide, or a protein encoded by a heterogeneous nucleotide. Recombinant cell can express a gene or a gene fragment in a form of a sense or antisense, that are not found in natural state of cell. In addition, a recombinant cell can express a gene that is found in natural state, provided that said gene is modified and re-introduced into the cell by an artificial means.

According to the present invention, a gene encoding a guanylyl cyclase, a gene encoding cGMP receptor protein, and a regulatory nucleotide sequence to which cGMP receptor protein binds may be inserted to a recombinant expression vector. The term "recombinant vector" means a bacterial plasmid, a phage, a yeast plasmid, a plant cell virus, a mammalian cell virus, or other vector. In a broad sense, any plasmid or vector can be used if it can replicate and be stabilized in a host. The important characteristic of the aforementioned expression vector is to have a replication origin, a promoter, a marker gene, and a translation control element.

The expression vector which includes a gene encoding a guanylyl cyclase, a gene encoding cGMP receptor protein, and a regulatory nucleotide sequence to which cGMP receptor protein binds and also a suitable transcriptional/translational regulatory signal may be constructed according to a method well known to a person skilled in the art. Examples of the method include an in vitro DNA recombination technique, a DNA synthesis technique, and an in vivo recombination technique. The DNA sequence can be effectively linked to a suitable promoter in an expression vector for inducing mRNA synthesis. Further, the expression vector may contain a ribosome binding site as a translation initiation site and a transcription terminator.

The expression vector may preferably comprise at least one selective marker. Said selective marker is a nucleotide sequence having a property which allows selection by a common chemical method. Any gene which can be used for the differentiation of transformed cells from non-transformed cell can be a selective marker. Examples thereof include a gene resistant to antibiotics such as ampicillin, kanamycin, G418, bleomycin, tetracycline, hygromycin, and chloramphenicol, but not limited thereto.

The present invention also provides a host cell transformed with the aforementioned recombinant vector.

According to one embodiment of the present invention, the host cell may be *Escherichia coli*, but not limited thereto. In fact, any one known in the pertinent art to have stable and continuous cloning and expression of the vector of the present invention in prokaryotic cells can be used. Examples thereof include, *Bacillus* sp. strain including *E. coli* JM109, *E. coli* BL21, *E. coli* RR1, *E. coli* LE392, *E. coli* B, *E. coli*

X 1776, *E. coli* W3110, *Bacillus subtillus, Bacillus thuringiensis* and the like, and intestinal bacteria and strains including *Salmonella typhimurium, Serratia marcescens* and various *Pseudomonas* sp. etc.

In addition, when a eukaryotic cell is transformed with the vector of the present invention, *Saccharomyce cerevisiae*, an insect cell, a human cell (for example, CHO (Chinese hamster ovary) cell line, W138, BHK, COS-7, 293, HepG2, 3T3, RIN and MDCK cell line), a plant cell, and the like can be used as a host cell.

The present also provides a method for independent expression of a foreign gene without interfering with a biological circuit of a host cell by transforming a host cell with a recombinant vector having a foreign gene inserted to the aforementioned recombinant vector.

When a host cell is a prokaryotic cell, delivery of the vector of the present invention into a host cell can be carried out by $CaCl_2$ method, Hanahan's method (Hanahan, D., J. Mol. Biol., 166:557-580 (1983)) or an electroporation method, and the like. In addition, when a host cell is a eukaryotic cell, the vector can be introduced to a host cell by a microinjection method, calcium phosphate precipitation method, an electroporation method, a liposome-mediated transfection method, DEAE-dextran treatment method, or a gene bombardment method, and the like.

The present invention also provides a composition or a kit for enhancing expression of a foreign gene without interfering with a biological circuit of a host cell comprising, as an effective component, a recombinant vector characterized in that a gene encoding a guanylyl cyclase, a gene encoding cGMP receptor protein, and a regulatory nucleotide sequence to which cGMP receptor protein binds, which are derived from a microorganism, are recombined in at least one plasmid, or a recombinant vector characterized in that a gene encoding cGMP receptor protein and a regulatory nucleotide sequence to which cGMP receptor protein binds, which are derived from a microorganism, are recombined in at least one plasmid.

The recombinant vector comprised in the composition or kit according to one embodiment of the present invention can be a recombinant vector in which a gene encoding a guanylyl cyclase, a gene encoding cGMP receptor protein, and a regulatory nucleotide sequence to which cGMP receptor protein binds are recombined in one plasmid, a recombinant vector having each of them introduced to a separate plasmid, or a recombinant vector having two of them introduced to one vector while remaining one introduced to other separate plasmid. The composition or kit of the present invention comprises the aforementioned recombinant vector as an effective component, and according to transformation of a host cell with the recombinant vector, expression of a foreign gene can be enhanced without interfering with a biological circuit of a host cell.

The kit of the present invention can be manufactured by a method that is commonly used in the pertinent art.

The present also provides a method for determining an interaction between a bait and a prey, wherein the method comprises:

recombining at least one of a bait or a prey with each of the catalytic domain and ATP hydrolyzing domain of guanylyl cyclase consisting of the amino acid sequence of SEQ ID NO: 2 which is derived from a microorganism, followed by expression in *E. coli*, and detecting an interaction between a bait and a prey which have been expressed as above.

With regard to the method according to one embodiment of the present invention, it is a new two-hybrid method in which guanylyl cyclase is used in addition to the yeast two hybrid method of a related art. The method of the present invention includes a step of recombining any one of a bait or a prey with each of the catalytic domain and ATP hydrolyzing domain of guanylyl cyclase derived from a microorganism followed by expression in *E. coli*. For example, a bait can be recombined to the catalytic domain or a prey can be recombined thereto. Similarly, a bait can be recombined to the ATP hydrolyzing domain or a prey can be recombined thereto. In other words, the bait and prey can be recombined to any one of the catalytic domain and ATP hydrolyzing domain. The interaction between the expressed bait and prey can be detected after expressing the recombined bait and prey in *E. coli*. When an interaction between the bait and prey is shown from interaction detection, the catalytic domain and the ATP hydrolyzing domain of guanylyl cyclase bind to each other so that the guanylyl cyclase can have an activity. As a result, cGMP is produced from GTP, and the produced cGMP forms a complex with a cGMP-receptor protein for binding to a regulatory nucleotide sequence to which cGMP protein binds. Thus, expression of a reporter gene located at downstream of the regulatory nucleotide sequence is induced to express the reporter (for example, GFP).

On the other hand, when there is no interaction between a bait and a prey, the catalytic domain and the ATP hydrolyzing domain of guanylyl cyclase protein cannot bind to each other so that the guanylyl cyclase will not have an activity. As a result, cGMP is not produced from GTP, and without any cGMP, a complex with a cGMP-receptor protein is not formed so that there is no binding to a regulatory nucleotide sequence to which cGMP protein binds, and expression of a reporter gene located at downstream of the regulatory nucleotide sequence is not induced. As a result, the reporter (for example, GFP) is not expressed.

Thus, when the expression of a reporter is detected, it can be recognized that there is an interaction between a bait and a prey. On the other hand, when no expression of a reporter is detected, it can be recognized that a bait and a prey have no interaction. Accordingly, by using the two-hybrid system of the present invention, an interaction between a bait and a prey can be determined (see, FIG. 17).

The catalytic domain of guanylyl cyclase of the present invention consists of the $14^{th}$ amino acid to $197^{th}$ amino acid of the amino acid sequence of SEQ ID NO: 2 and the ATP hydrolyzing domain consists of the $221^{st}$ amino acid to $595^{th}$ amino acid of the amino acid sequence of SEQ ID NO: 2, but they are not limited thereto.

The present also provides a method for screening a prey which binds to a bait, wherein the method comprises:

recombining a bait gene with any one of the catalytic domain and ATP hydrolyzing domain of guanylyl cyclase protein consisting of the amino acid sequence of SEQ ID NO: 2 which is derived from a microorganism and recombining a prey gene as a subject for detection with the remaining domain followed by expression in *E. coli*, and detecting an interaction between a bait and a prey which have been expressed as above.

As using the cGMP dependent signal transduction system, the screening method of the present invention is a method capable of detecting efficiently an interaction between proteins even when the amount of interacting proteins is small or the proteins have a weak binding property.

Hereinbelow, the present invention is explained in detail in view of the examples. However, the following examples are for an illustration of the present invention only, and by no means the context of the present invention is limited to them.

EXAMPLES

Example 1. Production of Recombinant Vector Containing Independent Signal Transduction Circuit and Production of Transformant Introduced with Recombinant Vector To obtain the elements constituting a signal transduction circuit from *Rhodospirillum centenum* strain, chromosomes were extracted from the strain by using a kit for extracting DNA (Wizard® Genomic DNA Purification Kit, Promega, USA). Then, the purity was analyzed and concentration was determined according to common DNA manipulation techniques. By using the extracted chromosome as a template and a primer set of oligonucleotides, a polymerase chain reaction (PCR) was performed to amplify DNA fragments that are required for circuit operation. Since the polynucleotide encoding the guanylyl cyclase consists of a base having a size of 3,051 bp, PCR was performed by using two divided fragments. The primers used are as described in the following Table 1.

TABLE 1

Information of primer for PCR

| Gene | Primer | Nucleotide sequence (5'→3') (SEQ ID NO:) |
|---|---|---|
| Amplification of fragment 1 of guanylyl cyclase | Cyc1-F | CTGGGATCCATGGCGACGAGCGGAAGC AC (8) |
| | Cyc1-R | CAGTCGACGACACGGGCACCGACCCGC CAG (9) |
| Amplification of fragment 2 of guanylyl cyclase | Cyc2-F | TCGTCGACTGGCGGATGCACGCGATGC AGC (10) |
| | Cyc2-R | ATGGGCCCAAGCTTCTAGCGGCCGGCA GCCGGGAG (11) |
| Gene encoding cGMP receptor protein | CRP-F | CGGGGATCCTCTAGAGAATTCATTAAA GAG (12) |
| | CRP-R | CAGAAGCTTTCAGCCGGCGAGCTT (13) |
| $P_{CEM}$ promoter | P-F | ATAAAGCTTATAGGGGGATCCGCG (14) |
| | P-R | ATGCGATCCTCTCATTCTAGAGGATCC CCG (15) |
| cyd2 | 0896-F | ATAGTGCACAGGCGACAGGCTCACGG ATG (16) |
| | 0896-R | TTCTCCTTTACTCATGACACCCTTCCCT GCCCGAC (17) |
| pyrC' | 1525-F | TTCTCCTTTACTCATTGGCTTTCCTCCT TTTTCGG (18) |
| | 1525-R | TATGAATTCGGGTCCGGGACTATGGC TTC (19) |
| cheY3 | 2133-F | TTCTCCTTTACTCATCGCTTCCCCCGT GGATGCGC (20) |
| | 2133-R | TATGAATTCACCGCCGCCGGCCCCAT CCG (21) |
| cstS1 | 2847-F | TTCTCCTTTACTCATAGGCTCGGCTCG CTGGAACG (22) |
| | 2847-R | TATGAATTCACCGGCCCGGCCTGACC GGC (23) |

For the PCR reaction, 8 ng of the chromosome DNA was used as a template, 1 μl of each primer solution described above (10 pmole concentration), 2 μl of dNTP in which each of dATP, dGTP, dTTP and dCTP is contained at 2.5 mM, 4 μl of 10× buffer solution, and 0.4 μl of 2.5 U/μl heat-resistant DNA polymerase (Speed-Pfu polymerase, Nanohelix, Korea) were admixed with another, and after adding sterilized water to have total amount of 40 μl, it was used as a reaction solution. After pre-heating the reaction solution for 10 minutes at 98° C., PCR was performed for 30 cycles in total in which one cycle includes 30 seconds at 98° C., 40 seconds at 52° C., and 30 seconds to 1 minute and 10 seconds at 72° C. depending on the length of DNA for extension. The amplified DNA fragments were collected from an agarose gel, and each was sub-cloned depending on the purpose according to the following method.

First, in case of the guanylyl cyclase, Cyc1 gene fragment which has been amplified by using Cyc1-F and Cyc1-R was digested with restriction enzymes BamHI and SalI, and Cyc2 gene fragment which has been amplified by using Cyc2-F and Cyc2-R was digested with restriction enzymes SalI and HindIII. Then, they were inserted to pTrc99a vector which has been digested with restriction enzymes BamHI and HindIII, and thus the recombinant vector pTrc99a-Cyc was produced.

Figure 2:
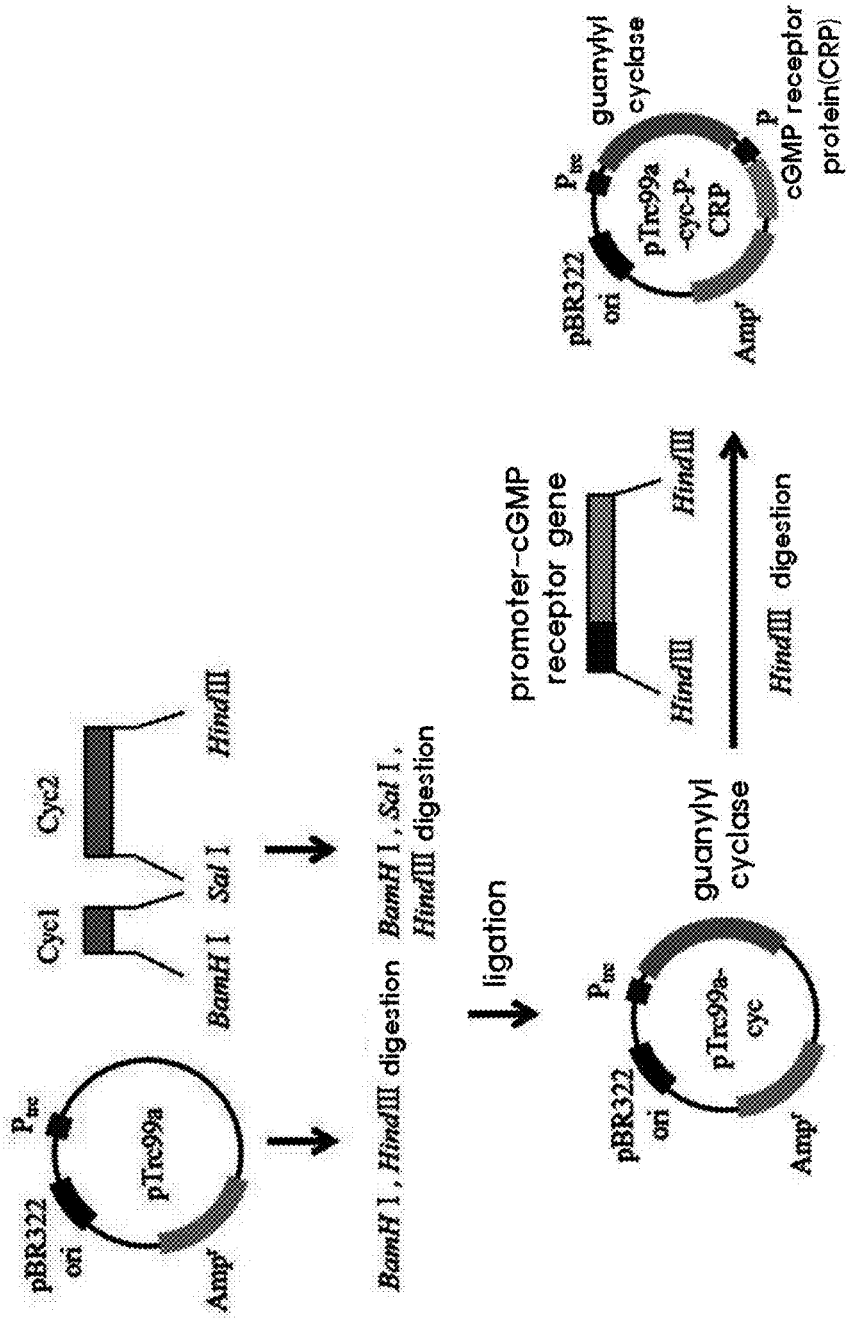
FIG. 2 is a schematic diagram illustrating a process of cloning guanylyl cyclase, which is an essential gene constituting the cGMP-dependent orthogonal signal transduction system and cGMP receptor protein, and a recombinant vector produced therefrom.

In case of the polynucleotide encoding cGMP receptor protein, a gene amplified by using CRP-F and CRP-R primers was obtained, and by performing overlapping PCR with constitutive trc promoter sequence which has been amplified by using P-F and P-R primers, the constitutive trc promoter-cGMP receptor fusion gene was obtained. The amplified gene fragment was digested with a restriction enzyme HindIII and inserted to pTrc99a-Cyc vector. Accordingly, pTrc99a-Cyc-P-CRP was produced (FIG. 2).

In order to confirm the expression of a foreign protein caused by transcription induction activity of the elements of the signal transduction circuit, a gene containing polynucleotide encoding the fluorescent protein GFPuv was produced to have a structure as described below. The primers used are as described in the following Table 2.

TABLE 2

Information of primer for PCR for synthesis of GFPuv gene

| Gene | Primer | Sequence information (5'→3') |
|---|---|---|
| cyd2-GFP | 0896 G-F | GTCGGGCAGGGAAGGGTGTCATGAGTAA AGGAGAA (SEQ ID NO: 24) |
| | 0896 G-R | GCGGAATTCTTATTTGTAGAGCTCATCCA (SEQ ID NO: 25) |
| pyrC'-GFP | G-F | CGGGTGCACTTATTTGTAGAGCTCATCCA (SEQ ID NO: 26) |
| | 1525 G-R | CCGAAAAAGGAGGAAAGCCAATGAGTAA AGGAGAA (SEQ ID NO: 27) |
| cheY3-GFP | G-F | CGGGTGCACTTATTTGTAGAGCTCATCCA |
| | 2133 G-R | GCGCATCCACGGGGGAAGCGATGAGTAA AGGAGAA (SEQ ID NO: 28) |
| cstS1-GFP | G-F | CGGGTGCACTTATTTGTAGAGCTCATCCA |
| | 2847 G-R | CGTTCCAGCGAGCCGAGCCTATGAGTAAA GGAGAA (SEQ ID NO: 29) |

Figure 3:
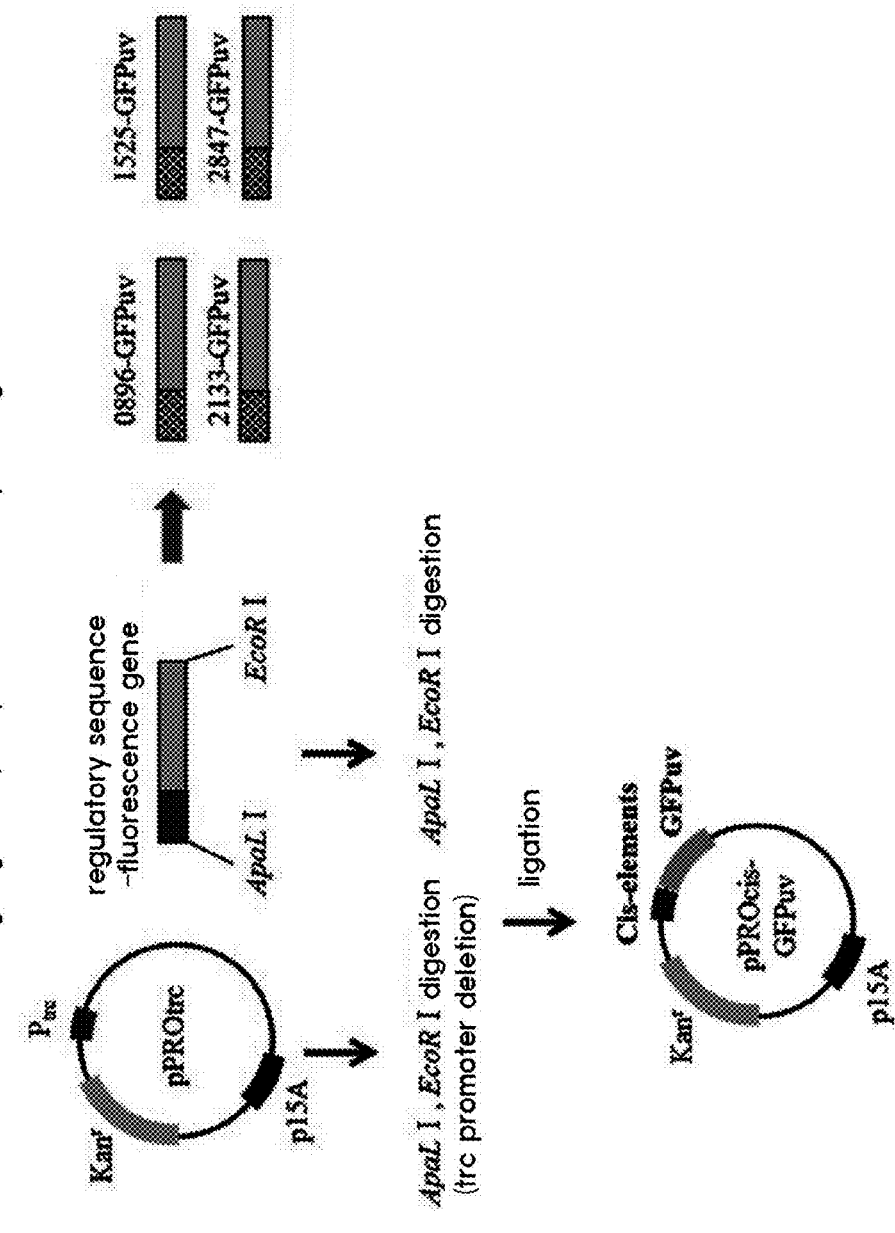
FIG. 3 is a schematic diagram illustrating a reporter fusion process for determining the function of a regulator sequence which is recognized, as an expression regulation factor of the cGMP-dependent orthogonal signal transduction system, by cGMP-receptor protein for inducing transcription.

By using GFPuv fragment having a sequence fused to the four regulatory sequences (denoted as number, 0896, 1525, 2133 and 2848) which have been amplified in previous steps, overlapping PCR was performed. The amplified DNA was treated with restriction enzymes ApaLI and EcoRI, and inserted to pPROtrc vector derived from pTrc99a, which has been digested with the same enzymes as above to prepare a construct (pPRO0896-GFPuv, pPRO1525-GFPuv, pPRO2133-GFPuv and pPRO2847-GFPuv), and it can be used for determining the expression of GFPuv according to binding of cGMP-receptor complex (FIG. 3). Because trc promoter is present in the vector of pPROtrc plasmid itself, trc promoter in the vector was removed by a treatment with restriction enzymes of ApaLI and EcoRI to confirm the activity of inducing GFP expression caused by the inserted regulatory sequence. Such constructs were analyzed in terms of stability and insert sequence after transformation of *E. coli* XL1-Blue as a host by CaCl$_2$ method or a method treating with FSB (frozen storage buffer) solution, and then used for the activity evaluation.

Figure 4:
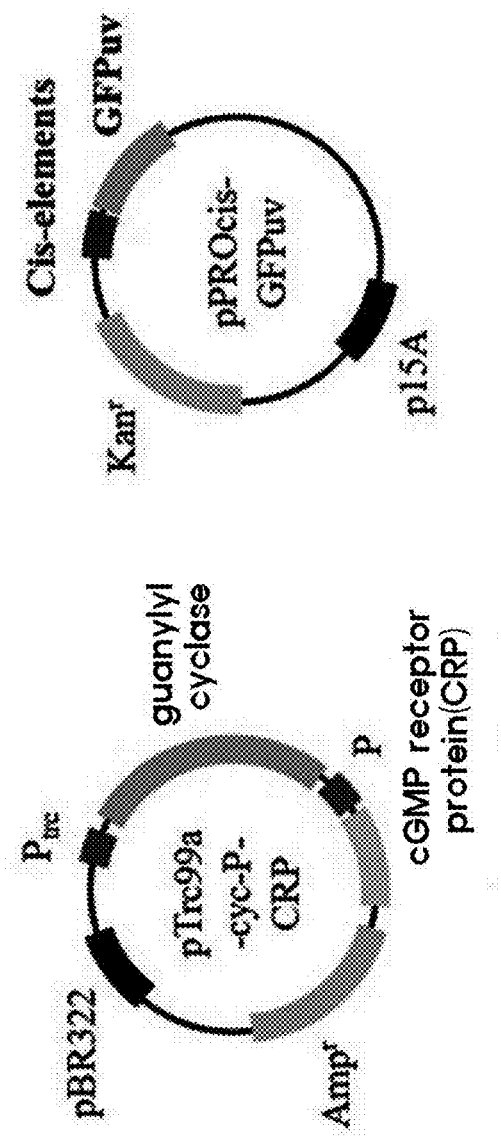
FIG. 4 is a schematic diagram illustrating the final product of a dual vector system for evaluating the cGMP-dependent orthogonal signal transduction system of the present invention. The two vectors have all the constitutional elements that are required for stable co-presence in one host.

Example 2. Evaluation of Inducing Expression of Foreign Gene by Signal Transduction Circuit Having Orthogonal Property In order to confirm whether the prepared orthogonal signal transduction circuit has an ability of inducing transcription in cGMP dependent manner, a signal transduction circuit module in dual vector form was introduced to a single host (FIG. 4). The model for evaluation of orthogonal signal transduction circuit consists of a plasmid (pTrc99a-Cyc-P-CRP) in which genes of guanylyl cyclase and cGMP-receptor protein are inserted and a plasmid (pPROcis-GF-Puv) to which a regulator sequence for binding with cGMP receptor protein and reporter are fused, and it is a system for inducing expression of a green fluorescence gene (reporter) according to transformation of a GTP molecule in a living body to cGMP molecule according to expression of guanylyl cyclase caused by IPTG induction and an action of the receptor protein which binds to cGMP.

*E. coli* having a dual vector was produced by electric shock transformation based on a method described before. Specifically, *E. coli* XL1-Blue was transformed with pTrc99a-Cyc-P-CRP in which genes encoding guanylyl cyclase and cGMP receptor protein are introduced, and the transformed single colony was cultured in a LB medium containing ampicillin (50 μg/ml) at conditions including 37° C. and 200 rpm. When the absorbance (OD$_{600}$) of the culture solution reaches 2.0, *E. coli* cells were inoculated to have 1% concentration of original culture medium. After the induced culture, when OD$_{600}$ has a value of 0.5, the cells were washed twice with cold 10% glycerol to prepare electrocompetent cells. To 20 μl of the cells, each plasmid of pPRO0896-GFPuv, pPRO1525-GFPuv, pPRO2133-GFPuv and pPRO2847-GFPuv was added in an amount of 5 to 10 ng and loaded on an apparatus for electroporation (Bio-Rad, USA). By applying electric current of 2.5 kV for 4.8 ms, transformation was performed. After that, 1 ml of SOC medium (0.5% Yeast Extract, 2% trypton, 10 mM NaCl, 2.5 mM KCl, 10 mM MgCl$_2$, 10 mM MgSO$_4$ and 20 mM glucose) was added and the cells were cultured for 1 hour at 37° C. After plating, clones exhibiting resistance to ampicillin and kanamycin were selected. As a control, cells that are prepared by adding pPROtrc empty vector with trc promoter to cells containing pTrc99a-Cyc-P-CRP vector were prepared.

(1) Culture and Growth Analysis of Microbial Cells

When grown in minimal medium (M9) added with 0.4% glucose, *E. coli* cells (will be employed as a host cell for evaluation of orthogonal signal transduction circuit activity) are known to show increased concentration of cellular GTP, i.e., up to 4.9 mM. Further, because it is known that the increased guanosine tetraphosphate (ppGpp) known as a representative starvation signal transducer in a microorganism inhibits GTP synthesis, to have a large amount of cGMP molecule required for producing orthogonal signals from GTP molecule, the host cells should be cultured under conditions in which nutrients (amino acids and carbon sources) are not deficient. As such, to reduce the stress-causing factors originating from an environment or nutrients, host cells equipped with signal transduction circuit are grown in a nutrient medium (LB) just before the entry to a stationary phase and then used for the experiment.

Figure 5:
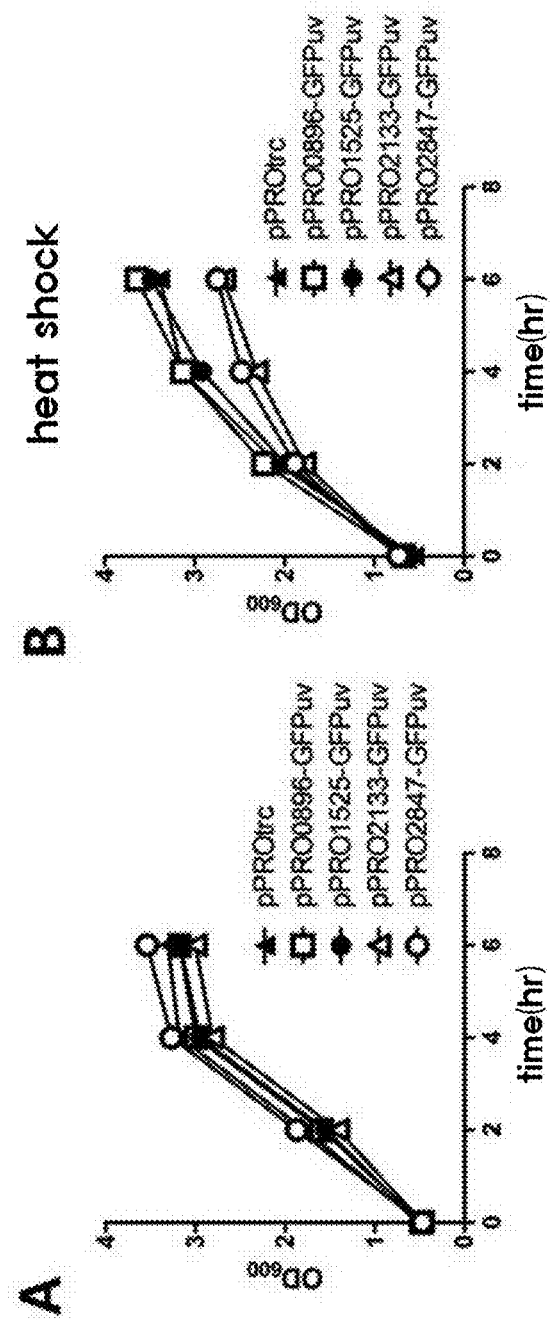
FIG. 5 is a drawing illustrating the cell growth inhibition and an ability to overcome stress caused by the recombinant vector which is introduced to a host for evaluating the cGMP-dependent orthogonal signal transduction system of the present invention. "A" shows that there is no inhibited cell growth of the host and "B" shows that there is no difference in a responsive protein expression to stress.

*E. coli* single colony which has been selected from aforementioned process was pre-cultured in a LB medium containing ampicillin (50 μg/ml) and kanamycin (50 μg/ml) at conditions of 37° C. and 200 rpm. When the absorbance (OD$_{600}$) of the culture reaches 2.0, the culture was re-inoculated to 1% concentration of the original culture. Then, when the absorbance reaches 0.5, it was treated with 0.1 mM IPTG to induce expression of guanylyl cyclase for 6 hours. The cells were sampled at an interval of 2 hours and the cell growth level was examined by measuring OD$_{600}$. As a result, the cell growth of host cells having orthogonal signal transduction genes was shown to exhibit the properties that are very similar to those of a host having an empty vector as a control group. Thus, it was confirmed that there is no growth delay or inhibition caused by replacement of a promoter or introduction of foreign genes (FIG. 5A). Further, among the sigma factors capable of binding to the regulatory sequence containing cGMP-receptor complex binding site which has been previously found to have a sequence for binding to the sigma factors (RpoD, RpoN, RpoH) that are required for induction transcription, it is known that, those except RpoD are an alternative sigma factor which induces transcription in accordance with binding with a RNA polymerase when the cell growth is at stationary phase or there is nitrogen deficiency or heat shock stress. As such, to enhance the transcription activating signal by an alternative sigma factor which can bind to a regulatory sequence, heat shock (42° C.) was applied for 30 minutes or so after adding IPTG, and culture was continued at 37° C. As a result of measuring OD$_{600}$ of the culture at an interval of 2 hours, it was found that OD$_{600}$ is lowered by 0.1 to 0.2 just after applying heat shock compared to the control group. However, it was also found that the normal growth rate is attained as the culture time is extended (FIG. 5B). As such, it was able to confirm that, even when stresses are caused for enhancing the activity of orthogonal factors or enhancing the signals, there is no significant problem in cell growth.

(2) Measurement of Activity of Orthogonal Signal Transduction Circuit for Expression of Foreign Gene To compare the expression level of cGMP-dependent induction in the aforementioned five transformed microbial strains (all of them commonly has pTrc99a-Cyc-P-CRP vector, and each is a clone introduced with pPRO0896-GFPuv, pPRO1525-GFPuv, pPRO2133-GFPuv, pPRO2847-GFPuv or pPROtrc vector) as a subject, culture and heat shock application were performed as described above. The cell culture was sampled at an interval of 2 hours and the culture sample was subjected to high-speed centrifuge (13,000 rpm) to collect the cells. The cells were washed with distilled water and suspended in a 50 mM Tris-Cl (pH 7.9) buffer. The prepared sample was mixed with cell lysis solution (50 mM Tris-CI, 150 mM NaCl, 1 mM DTT, 5% glycerol, 1 mM EDTA, 0.1% SDS, pH 7.9) at ratio of 1:1. After the reaction for 15 minutes, the fluorescence of the sample was measured by a fluorimeter (Infinite M200, Tecan, Switzerland).

Figure 6:
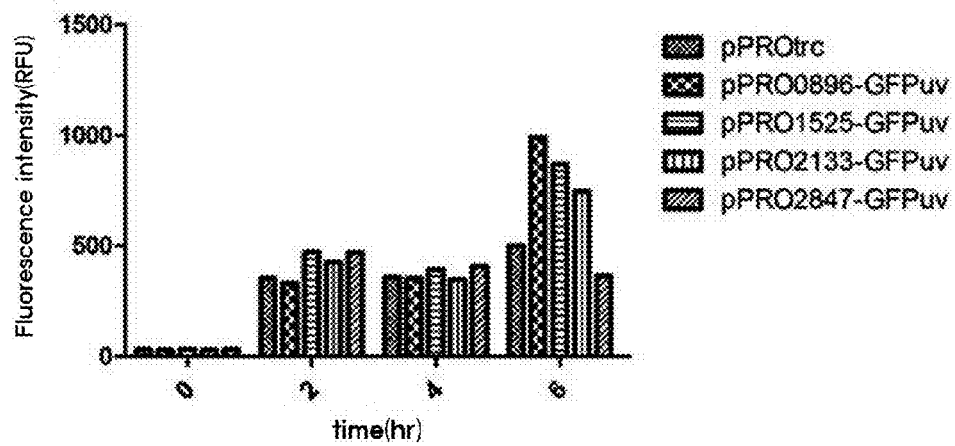
FIG. 6 shows a result of comparing an expression amount of a reporter by inducing protein expression at different cell concentration in order to evaluate the cGMP-dependent orthogonal signal transduction system of the present invention. The relatively low fluorescence indicates the result obtained by using a small amount of cells. A fluorescence value from the control group indicates that the fluorescence is measured intrinsically at basal level by using whole cells.
Figure 6:
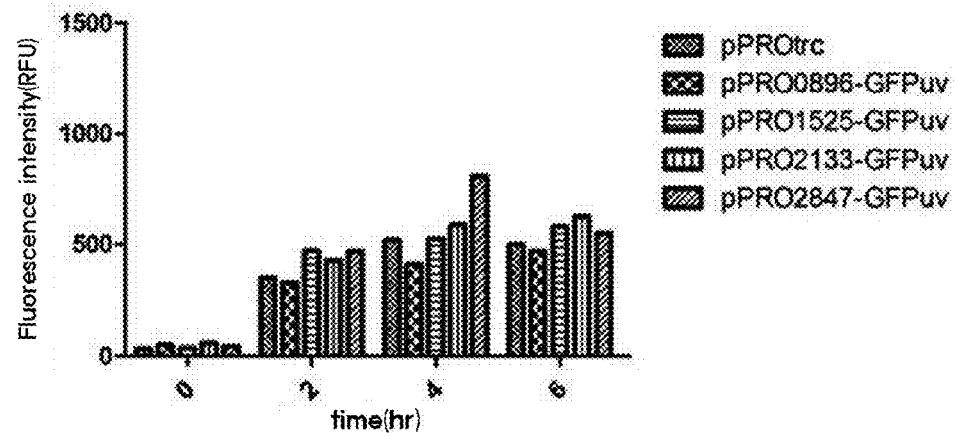
Figure 7:
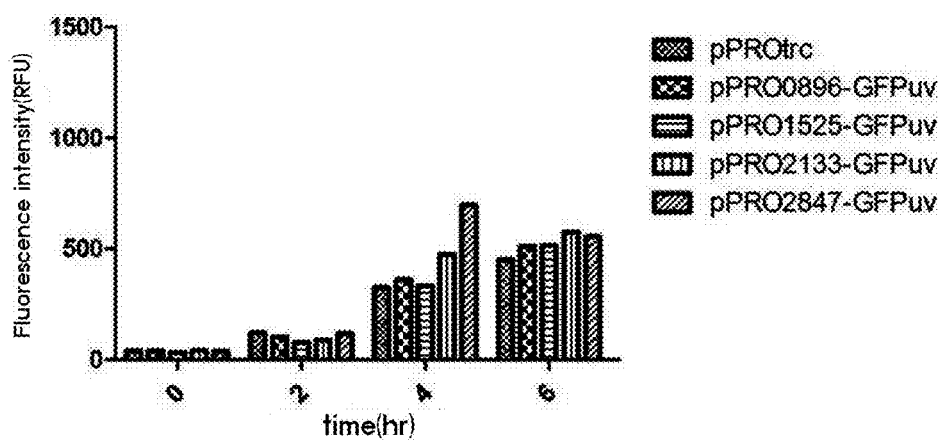
FIG. 7 shows a result of comparing an expression amount of a reporter after application of heat shock in order to determine a relationship between a sigma factor, which binds to a regulatory sequence related to orthogonal signal reception in the cGMP-dependent orthogonal signal transduction system of the present invention, and a stress response. A possibility was confirmed from the $4^{th}$ regulatory sequence.

As a result, in case of not applying any heat shock, the observed fluorescence was at almost the same level as that of the control group, up to four hours after adding IPTG. However, after six hours, the cells having pPRO0896-GFPuv, pPRO1525-GFPuv or pPRO2133-GFPuv were confirmed to show higher fluorescence than the control group (FIG. 6). In case of pPRO2847-GFPuv, the fluorescence was similar to that of the control group, but it has a characteristic that the fluorescence increases only right after adding IPTG. As such, it is believed that the type of the sigma factor binding to a regulatory sequence is different or there is a difference in binding force. When heat shock is applied, only pPRO2133-GFPuv or pPRO2847-GFPuv having RpoH binding site and pPRO0896-GFPuv having RpoD binding site exhibited higher fluorescence than the control group (FIG. 7). Because they are the results only when the mined orthogonal signal transduction circuit produces cGMP based on a cyclase activity and then induces transcription after forming a complex with a receptor which binds to cGMP, it is suggested that expression of a foreign protein can be achieved by using the elements constituting the signal transduction circuit. The relatively low fluorescence indicates the result from a sample which has been used in a small amount, and thus this problem can be easily solved by controlling the sample amount or enhancing the cyclase activity (i.e., expression level of the wild type protein is extremely low). As more direct evidence, the activity of a cyclase or cGMP concentration-dependent induction of a reporter expression can be easily observed by using a fluorescence microscope or a FACS (fluorescence-activated cell sorter). After confirming again the activity of the orthogonal signal transduction system for inducing transcription (i.e., reporter expression) according to the aforementioned processes, the next experiments were performed.

Example 3. Evaluation of No Interference/Independent Operational Activity of Orthogonal Signal Transduction Circuit As shown in the aforementioned Example 2, when a signal transduction circuit capable of regulating transcription is obtained from heterogeneous cells and operated in *E. coli*, it was confirmed that the expression of a reporter gene is induced. Because guanylyl cyclase, cGMP receptor protein, or a regulator sequence binding to it, which are an element for constituting the circuit, are not present in *E. coli* and thus cannot be recognized as a signal transduction messenger, it is believed that, during a process of expressing the reporter as a product of transcription induction, it functions independently with no interference with a signal transduction system intrinsic to the host cell. In other words, because the activated signal is delivered by using cGMP, which is naturally not used in *E. coli*, as a signal for inducing transcription, there is no signal disturbance or interference caused by other proteins in the host, and thus all of the generated activating signal (cGMP) contribute to induction of foreign protein expression. However, in case of trc promoter employed as an operation inducing factor of the orthogonal signal transduction circuit used in Example 2 (i.e., factor for inducing initial transcription for signal generation), there is a leaking higher than basal level so that a noise or a background is strong during the signal transduction process and it was found to be inappropriate for determining the signal strength and for examining whether or not all the generated activating signal (cGMP) is used for protein expression. As such, further experiments as described below were also carried out.

Figure 8:
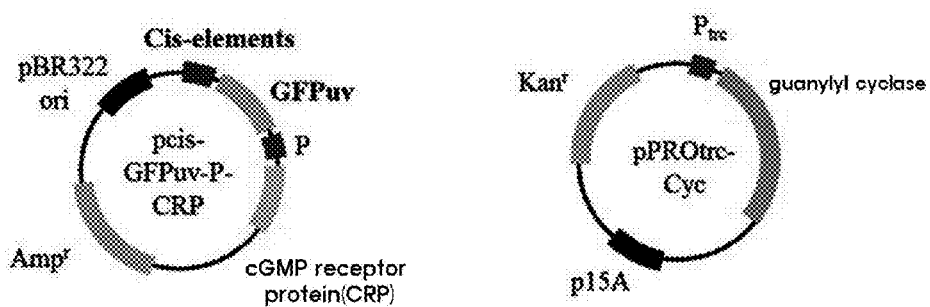
FIG. 8 is a vector diagram illustrating a cloned product obtained by fusion of a $P_{bad}$ promoter with strongly-regulated transcription for reducing a noise caused by leaking during the operational process of the cGMP-dependent orthogonal signal transduction system of the present invention.
Figure 8:
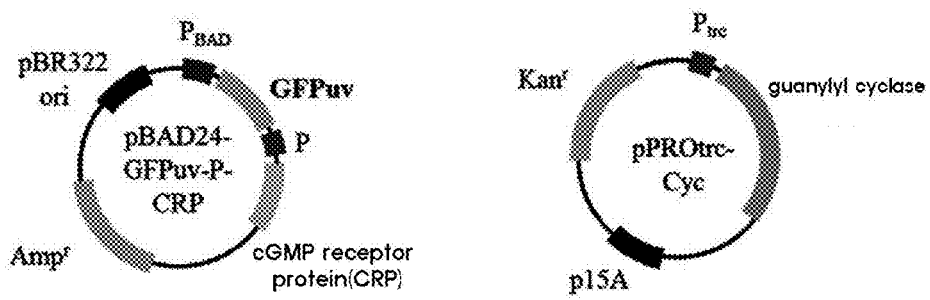

As a method to cope with the aforementioned problems, the regulatory sequence is moved to pBAD system which has relatively tighter regulation on expression than other systems for inducing expression and, to have compatibility with said vector, the polynucleotide encoding guanylyl cyclase was inserted to a plasmid which has an antibiotics marker and a replication origin that are different from those of pBAD vector. Further, to increase the accessibility of cGMP receptor protein to a regulatory sequence, a new orthogonal signal expression system in which a polynucleotide encoding constitutive $P_{CEM}$ promoter-cGMP receptor protein is located behind a reporter gene fused to a regulatory sequence was designed (FIG. 8). The designed recombinant vector was constructed according to the following processes.

DNA fragment of the gene encoding fluorescence protein GFPuv fused to four regulatory sequences was amplified by using a primer which contains a sequence recognizing restriction enzymes AgeI and HindIII. For inserting the amplified gene, pBAD24 vector was treated with restriction enzymes AgeI and HindIII to remove the $P_{BAD}$ promoter region. Further, according to cloning of the gene encoding fluorescence protein GFPuv fused with each regulatory sequence which has been digested with the same enzymes, vectors of p0896-GFPuv, p1525-GFPuv, p2133-GFPuv and p2847-GFPuv were prepared. As a control group, vector pBAD24-GFPuv in which a fluorescence gene is inserted at the downstream of $P_{BAD}$ promoter was prepared. Further, each vector of p0896-GFPuv, p1525-GFPuv, p2133-GFPuv, p2847-GFPuv and pBAD24-GFPuv was treated with restriction enzyme HindIII, and by inserting constitutive $P_{CEM}$ promoter-cGMP receptor polynucleotide which has been obtained by treating pTrc99a-Cyc-P-CRP plasmid with the same enzyme, yielding recombinant vectors of p0896-GFPuv-P-CRP, p1525-GFPuv-P-CRP, p2133-GFPuv-P-CRP, p2847-GFPuv-P-CRP and pBAD24-GFPuv-P-CRP. As a final step, pTrc99a-Cyc-P-CRP plasmid was treated with restriction enzymes BamHI and HindIII to obtain the polynucleotide encoding guanylyl cyclase and then cloned in pPROtrc vector which has been treated with the same enzymes. As a result, vector pPROtrc-Cyc was produced.

With regard to the orthogonal signal transduction circuit for confirming no interference/independent operation in a host, to produce a dual vector type system in the same manner as Example 2 above, a recombinant strain transformed with pPROtrc-Cyc plasmid was prepared first, and then introduced with each of p0896-GFPuv-P-CRP, p1525-GFPuv-P-CRP, p2133-GFPuv-P-CRP, p2847-GFPuv-P-CRP, or pBAD24-GFPuv-P-CRP plasmid to prepare a recombinant cell having two vectors (FIG. 8). *E. coli* cells exhibiting resistance to both ampicillin and kanamycin were selected from the transformants, and a single colony was inoculated to a nutrient medium LB. The cells were cultured according to the method described in Example 2, and after sampling, the fluorescence was measured.

Figure 9:
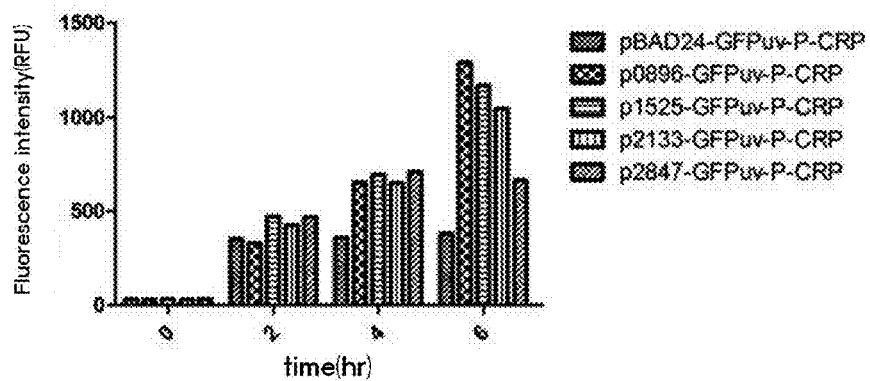
FIG. 9 shows a result in which the signal is strengthened and transcriptional product is more produced as a result of combining the cGMP-dependent orthogonal signal transduction system of the present invention with $P_{bad}$ promoter. Specifically, the characteristics of the orthogonal signal are exhibited well and a result sufficient for use as a signal for inducing protein expression is shown.
Figure 9:
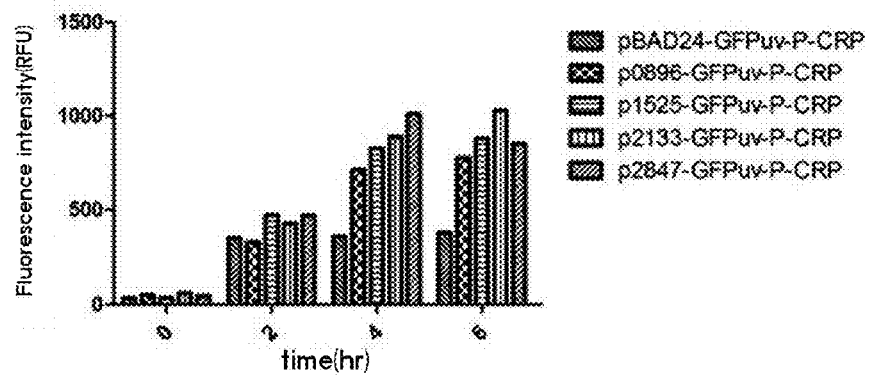

As a result, the observed fluorescence was at almost the same level as that of the control group, up to four hours after adding IPTG. However, after six hours, the transformants having p0896-GFPuv-P-CRP, p1525-GFPuv-P-CRP or p2133-GFPuv-P-CRP plasmid were confirmed to show higher fluorescence than the control group. In case of p2847-GFPuv-P-CRP, however, the fluorescence increased by adding IPTG when $OD_{600}$ is 0.7 (FIG. 9). Because the fluorescence from *E. coli* cells containing control plasmid remains low irrespective of the time, it was found that *E. coli* does not respond to cGMP which is produced by guanylyl cyclase expressed by addition of IPTG. Thus, it was found that cGMP-dependent induction of gene transcription is impossible in *E. coli* host. As such, it was proven that the signal transduction circuit established by the present invention is an orthogonal system which can operate independently from *E. coli*.

Figure 10:
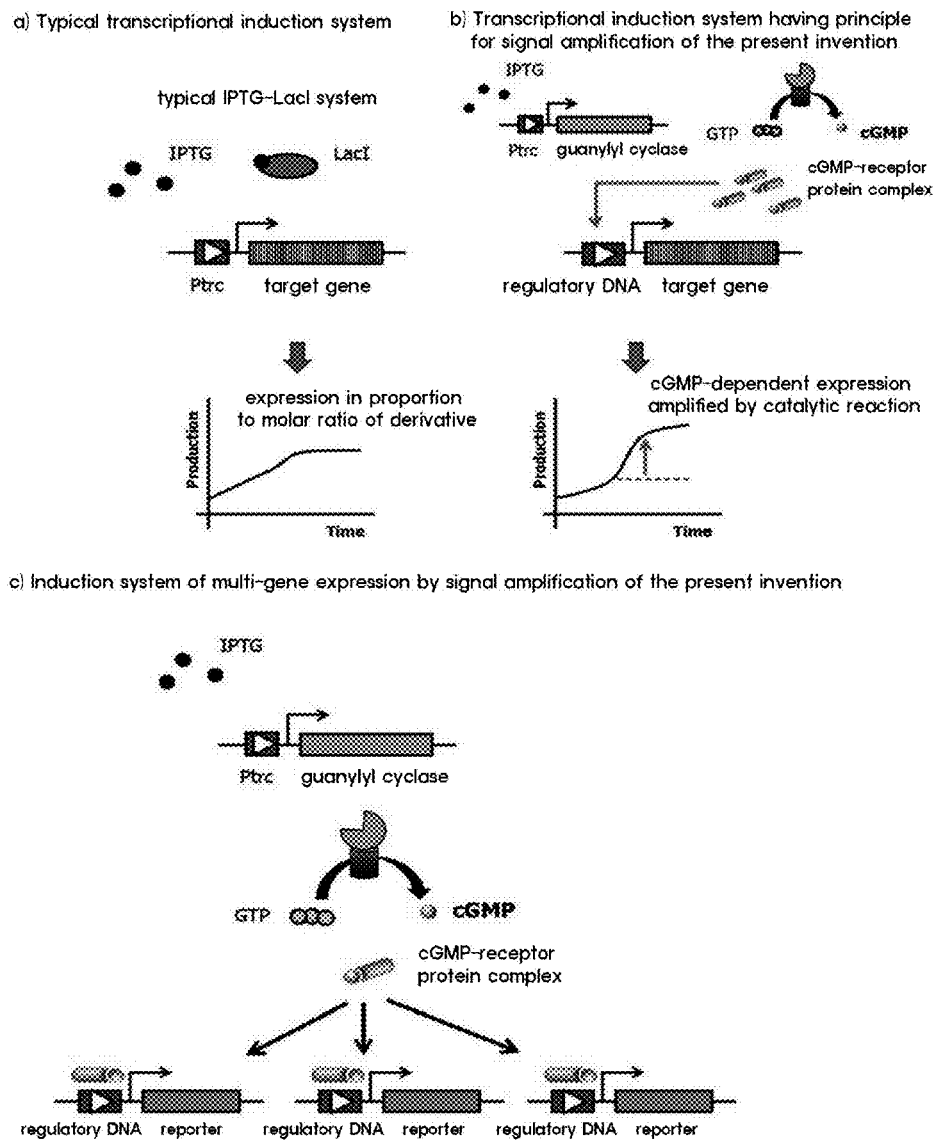
FIG. 10 includes schematic diagrams illustrating and comparing the advantages of related systems, i.e., (a) transcriptional induction system in which only typical inducing agents of a related art are used, (b) principle for signal amplification including secondary messenger (cGMP), which is adopted by the cGMP-dependent orthogonal signal transduction system of the present invention, and (c) simultaneous expression of multiple genes (operon) can be achieved by using the aforementioned principle even with a weak input signal.

Example 4. Amplification of Signal for Activating Transcription by Orthogonal Signal Transduction System As shown in the above, by regulating the transcriptional activity by using cGMP which is not utilized as a signal transducer in E. coli host itself, a circuit not overlapped with the signal transduction system intrinsic to the host was produced and the performance of the circuit was evaluated. The produced circuit not only has an independent signal transducing activity but also operates the circuit by using cGMP as a product of enzyme activity. As such, it is believed to have a function of signal amplification. Namely, when given with little input signal at initial stage of the reaction (i.e., compounds that are required for inducing synthesis of a limited amount of guanylyl cyclase), synthesis of guanylyl cyclase is induced, and an excess amount of cGMP corresponding to catalytic turnover (Kcat) can be produced within several minutes even when the amount of expressed enzyme is small. As such, the gene expression regulated by cGMP has an overexpressing property compared to the initial input signal, and thus, the amplification of an initial signal is achieved by cGMP, which is a second signal messenger (FIG. 10). Further, it is believed that the orthogonal signal transduction system enables induction of simultaneous expression of several genes having regulatory sequence of which transcription is induced by a second messenger, thus having capability of multiple genes or operon expression. Thus, it can be an example which artificially and also orthogonally achieves a naturally occurring global regulation mechanism in which a second messenger is involved during a signal transduction cascade included in many natural biological gene circuits or signal transduction circuits.

In order to confirm the signal amplification effect, pPRO0896-GFPuv plasmid (i.e., containing a regulatory sequence) which has been shown to have the highest activity by cGMP in the above example was selected and a polynucleotide encoding a green fluorescent gene fused with the same regulatory sequence is consecutively inserted to the terminal of the green fluorescence gene. As a result, a system having three reporters was designed. In order to exclude an effect of the regulatory sequence at the first position (i.e., a phenomenon in which transcription of the second gene starts without finishing the transcription of the first gene), a method as follows was devised: 200 bp of an intervening nucleotide sequence is inserted behind the first fluorescence gene, and in order to lower the effect of the second regulatory sequence, the third regulatory sequence and the target gene are inserted in an opposite direction. The experiments were performed as follows.

Figure 11:
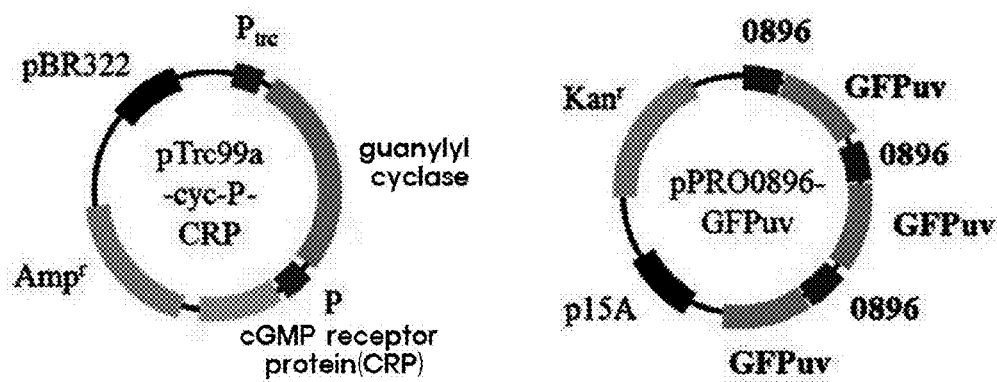
FIG. 11 is a schematic diagram illustrating an evaluation system which is used for monitoring the signal amplification effect as an advantage of the cGMP-dependent orthogonal signal transduction system of the present invention.

First, to prepare a circuit of dual vector type in the same manner as Example 2, a recombinant strain transformed with pPRO (0896-GFPuv)3 plasmid was prepared. Then, by introducing pTrc99a-Cyc-P-CRP plasmid thereto, a recombinant strain having two vectors was prepared (FIG. 11). As a control group, a recombinant strain having pTrc99a plasmid from which guanylyl cyclase and cGMP receptor protein are removed and pPRO (0896-GFPuv)3 plasmid, a recombinant strain having pTrc99a-P-CRP plasmid from which only guanylyl cyclase is removed and pPRO (0896-GFPuv)3 plasmid, and a recombinant having only empty vector (pTrc99a, pPROtrc) were used. Among the transformants, clones exhibiting resistance to ampicillin and kanamycin were selected. A single colony was inoculated to a nutrient medium and pre-cultured at conditions of 37° C. and 200 rpm. The pre-culture solution was re-inoculated to 1% concentration of the original culture. Then, when the absorbance reaches 0.5, it was treated with 0.01 mM IPTG and cultured for 6 hours. The cell culture was then sampled.

Figure 12:
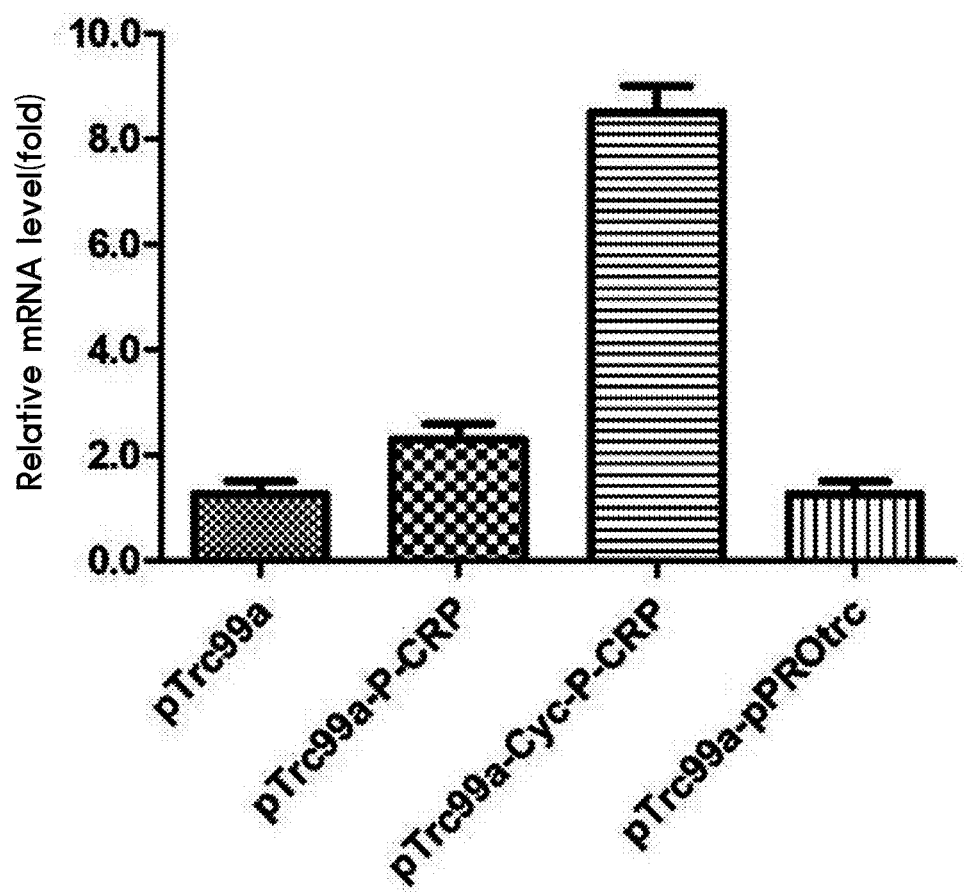
FIG. 12 shows a result of comparing the signal amplifying effect of the orthogonal signal transduction system of the present invention, in which the comparison is made at transcript level.

When the fluorescence of the sample was measured for the entire cells, the reporter expression amount was found to be 3.5 to 5 times higher than those of the control group. However, because there can be an additive effect based on the maturation time and stability of the fluorescent protein, an experiment for more directly comparing the amount of the transcript (by signal amplification) was carried out. To compare the amount of the transcript, a commercially available kit for RNA extraction (Easy-BLUE™ Total RNA Extraction Kit, Intron, Korea) was used to extract whole RNA from the sample. After synthesizing cDNA from it, the amount of the transcript of the fluorescence gene was quantified relatively compared to the control group by using the primers described below (FIG. 12). The primers that are used are as described in the following Table 3.

TABLE 3

Information of primer for quantitative RT-PCR

| Primer | Sequence information (5'→3') |
| --- | --- |
| GFPuv RT-F | CGCGTCTTGTAGTTCCCGTCA (SEQ ID NO: 30) |
| GFPuv RT-R | TGACAAGTGTTGGCCATGGAACA (SEQ ID NO: 31) |
| GapA RT-F | TGATCCGGCTAACCTGAA (SEQ ID NO: 32) |
| GapA RT-R | GCGGTGATGTGTTTACGA (SEQ ID NO: 33) |

Figure 13:
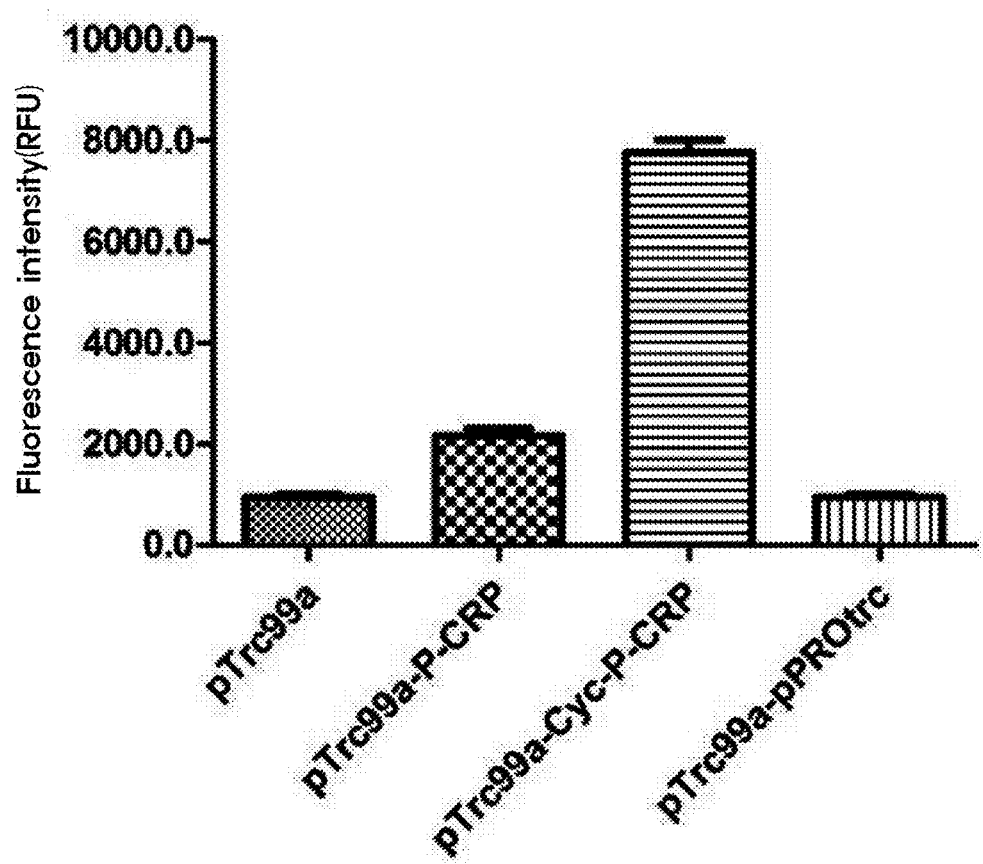
FIG. 13 shows a result of comparing the signal amplifying effect of the cGMP-dependent orthogonal signal transduction system of the present invention, in which the comparison is made based on the fluorescence exhibited by reporter expression.

As a result of quantifying the relative amount of mRNA of the fluorescence gene in the recombinant strain by using RT-PCR, it was found that the recombinant strain from which guanylyl cyclase and cGMP receptor protein have been removed has the mRNA at basal level, which is similar to the recombinant strain having an empty vector. When only guanylyl cyclase is removed, the amount of the transcript of the fluorescence gene was about two times higher than the recombinant strain having an empty vector. In case of the strain having both guanylyl cyclase and cGMP receptor protein, the amount of the transcript of the fluorescence gene was about eight times higher than the recombinant strain having an empty vector. These results are correlated with the result of measuring fluorescence from recombinant strains in the same manner as Example 2 above (FIG. 13). This result is believed to be based on the effect of cGMP which is produced only when guanylyl cyclase exists. Specifically, it is believed that, as a large amount of cGMP molecule activates cGMP receptor protein and maintains transcription induction, the fluorescent protein is produced in a large amount. Even with a trace amount of initial input signal (0.01 mM IPTG), overexpression of a reporter can be achieved due to a transcription activity amplifying effect based on production of a large amount of cGMP molecule. Accordingly, it is suggested that the system of the present invention can be effectively used for producing fermentation product or proteins with the target activity to various purpose.

As more direct comparison, further experiments were carried out in which, as a control group, each of the regulatory sequence-reporter fusion gene was replaced with Ptrac-reporter fusion gene of which transcription is induced at molar ratio by IPTG as an initial input signal. As a result, fluorescence at basal level was shown, and thus it was confirmed again that the effect shown in the present invention is a very effective means for signal amplification and multi gene or operon expression.

Example 5. Establishment of a System for Simultaneous Expression of Several Useful Foreign Genes (1) Simultaneous Expression of Industrial Enzymes To establish a system for simultaneous expression of several useful foreign genes based on orthogonal signal transduction, two fluorescence genes at downstream region of pPRO (0896-GFPuv)3 plasmid were replaced with polynucleotides which encode esterase and β-glucosidase, respectively. Specific methods for the experiment are as follows. To produce a dual vector system-based signal amplification circuit in the same manner as Example 4 above, a recombinant strain transformed with pPRO0896-GFPuv-0896-est-0896-glu plasmid was produced first. Furthermore, by introducing the other plasmid (pTrc99a-Cyc-P-CRP), a recombinant strain containing the two vectors was produced. As a control group, a microbial strain having pTrc99a empty vector from which genes encoding guanylyl cyclase and cGMP receptor protein have been removed was used. To confirm the gene expression in the produced strain, a transformed single colony of E. coli was pre-cultured in a LB medium containing ampicillin (50 μg/ml) and kanamycin (50 μg/ml) at conditions of 37° C. and 200 rpm. After inoculation to have 1% concentration of the original culture (15 ml), when the absorbance ($OD_{600}$) of the culture reaches 0.5, IPTG was added to 0.1 mM and expression of the green fluorescent protein, esterase, and β-glucosidase was induced for 6 hours. Six hours later, the cell culture was sampled and the fluorescence from the green fluorescent protein was measured in the same manner as Example 2. For the following two enzymes, a solid phase zymography was used for more accurate measurement. In case of the esterase, the obtained cells were suspended in a buffer solution (50 mM Tris-HCl, pH 8.0) and disrupted by using an ultrasonicator (Sonics and materials, USA). The prepared sample was subjected to centrifuge for fractionating soluble proteins, which were then electrophoresed by 8% Native-PAGE. Then, after adding the substrate solution (α-naphthyl acetate, Fast Blue RR), the reaction was allowed to occur for 20 minutes at room temperature. In case of the β-glucosidase, the soluble proteins were electrophoresed by 8% Native-PAGE. Then, after adding a buffer solution containing 1 mM MUG as a substrate, the reaction was induced for 1 hour in a shaker at 37° C. (200 rpm).

Figure 14:
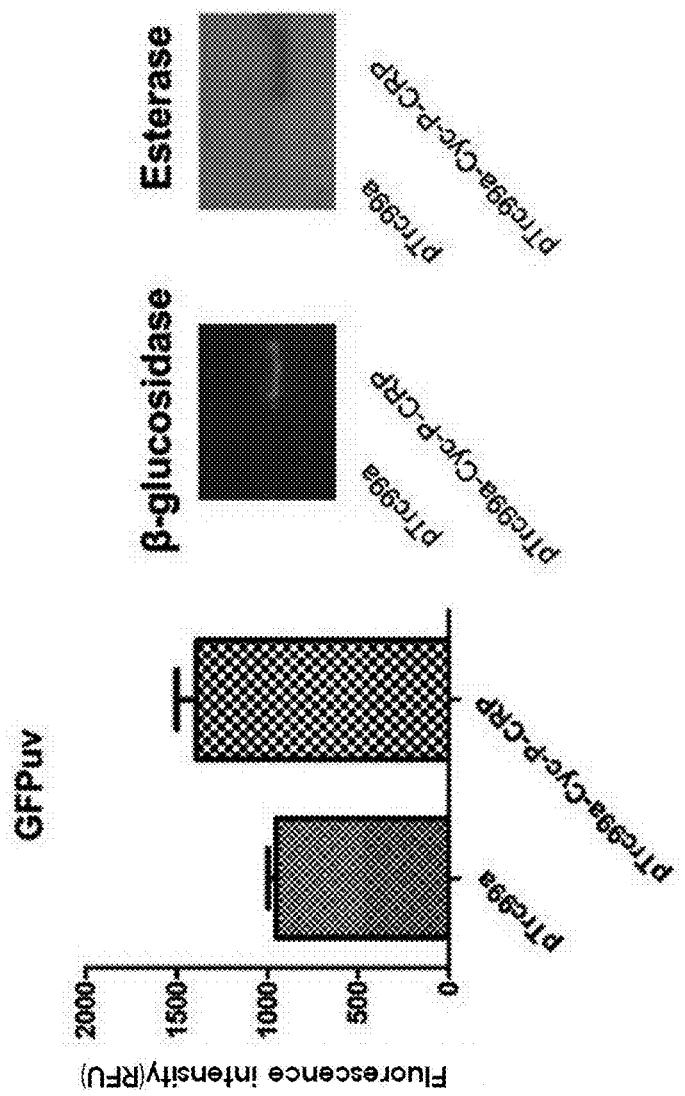
FIG. 14 shows a product of simultaneous expression of multiple genes of which regulatory sequence is fused via a signal amplified by the cGMP-dependent orthogonal signal transduction system of the present invention. Specifically, after inducing simultaneous expression of a fluorescent protein reporter and two kinds of an industrial enzyme for evaluation of operation, functional overexpression of the industrial enzymes was confirmed by zymogram.

As a result, overexpression of the green fluorescent protein, ester hydrolase, and β-glucosidase was confirmed. In particular, unlike a common method for expression, an excellent expression property that functional overexpression is induced simultaneously by cGMP to the extent that the enzyme activity of disrupted cell product of which expression has been induced for 6 hours can be observed with a naked eye (FIG. 14).

Figure 15:
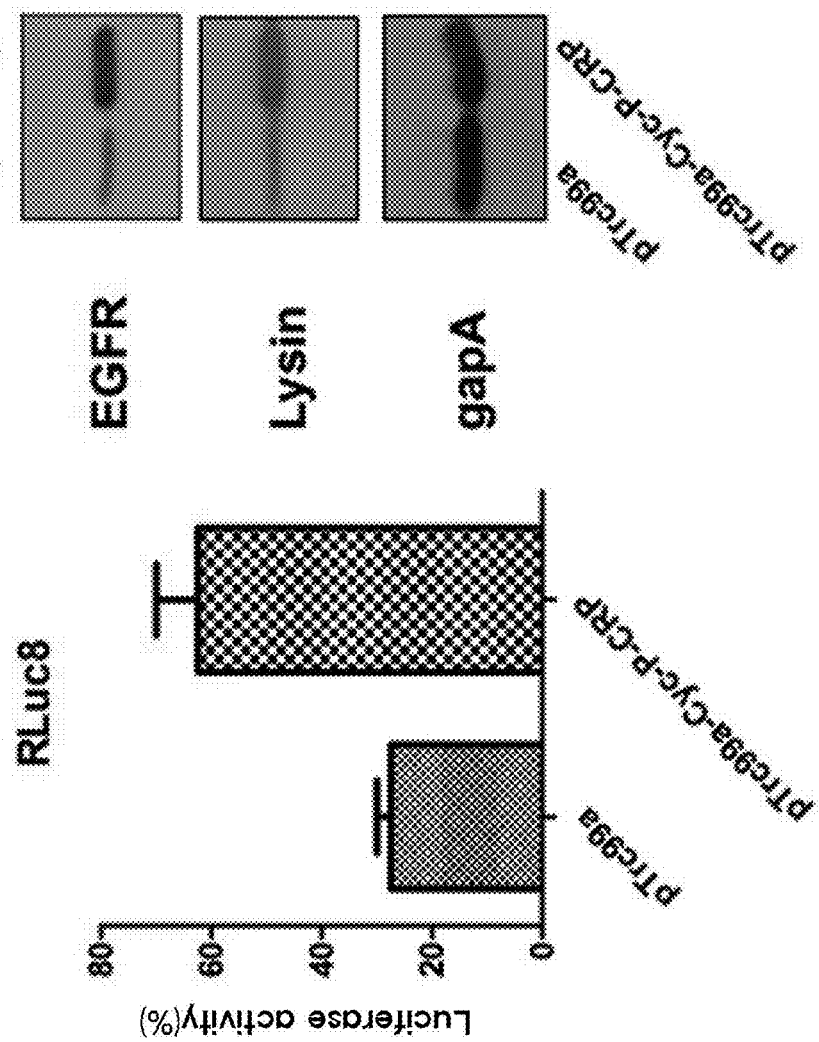
FIG. 15 shows a product of simultaneous expression of multiple genes of which regulatory sequence is fused via a signal amplified by the cGMP-dependent orthogonal signal transduction system of the present invention, in which co-expression of a pharmaceutical protein used for treatment of intractable cancers is shown. Specifically, after inducing simultaneous expression of a reporter and two kinds of an enzyme for pharmaceutical use, functional overexpression was confirmed by Western blot using an antibody.

(2) Determination of Simultaneous Expression of Cancer Cell Target and Cell Lysis Gene Next, it was determined whether or not the simultaneous expression effect of cGMP is applicable to a pharmaceutical which is hardly expressed in E. coli and not suitable for simultaneous expression. As an example, expression of an artificial antibody and holin/lysin, which has a cancer cell target and a cell lysis function, respectively, was tried. To do so, the polynucleotide encoding Renilla luciferase is inserted behind the regulatory sequence of 0896 to produce pPRO0896-RLuc8 plasmid. Further, by inserting the polynucleotides which encode an artificial antibody recognizing epidermal growth factor receptor (EGFR) as a representative cancer biomarker or a factor for inducing cell lysis in the same manner as pPRO0896-GFPuv-0896-est-0896-glu vector of Example 5 above, a new construct (pPRO0896-RLuc8-0896-EGFR-0896-lysin) was prepared. At that time, by using pTrc99a-Cyc-P-CRP plasmid like Example 5, simultaneous expression of the gene based on a dual vector system was induced. As a control, an empty vector (pTrc99a) not inserted with guanylyl cyclase and cGMP receptor protein was used. The transformed strain was cultured according to the same conditions as Example 5, and the luciferase activity from the cell lysis solution was measured. The bacteria sample required for luminescence measurement was diluted by ×1000 to prevent signal saturation. By dissolving the prepared bacteria sample for 20 minutes in 5× lysis solution (Promega, USA) followed by addition with coelenterazine (4 μg/ml) as a substrate, the luminescent signal was measured by using a luminometer. Further, by using an antibody which recognizes artificial antibody and an antibody which recognizes the cell lysis factor holin/lysin, Western blot was performed according to a known method (FIG. 15).

As a result, unlike the control group in which luminescence at basal level is shown, E. coli producing cGMP exhibited a high amount of luminescence which is close to saturation level. As a result of Western analysis for measuring expression of two different genes, bands corresponding to the antibody recognizing EGFR-binding artificial antibody and the antibody having selectivity for the cell lysis factor were clearly detected. Thus, it was confirmed that the orthogonal signal transduction system using cGMP molecules as a second signal messenger can be also used for expression of proteins with high added value like a pharmaceutical gene. These results suggest that, when a therapeutic microorganism having the orthogonal signal transduction system is loaded with a pharmaceutical gene and applied in vivo, solid cancer targeting can be achieved by an artificial antibody which recognizes EGFR, and also an effective system enabling both functions of probing/treatment by simultaneously expressed pharmaceutical protein can be established. Because there is also a signal amplifying effect, it has a value as a prototype of a new drug delivery system in which only an extremely low level of input signal is required from outside for triggering (i.e., inducing agent for expressing cyclase).

Example 6. Inducible Expression System Using cGMP as Inducing Agent

Figure 16:
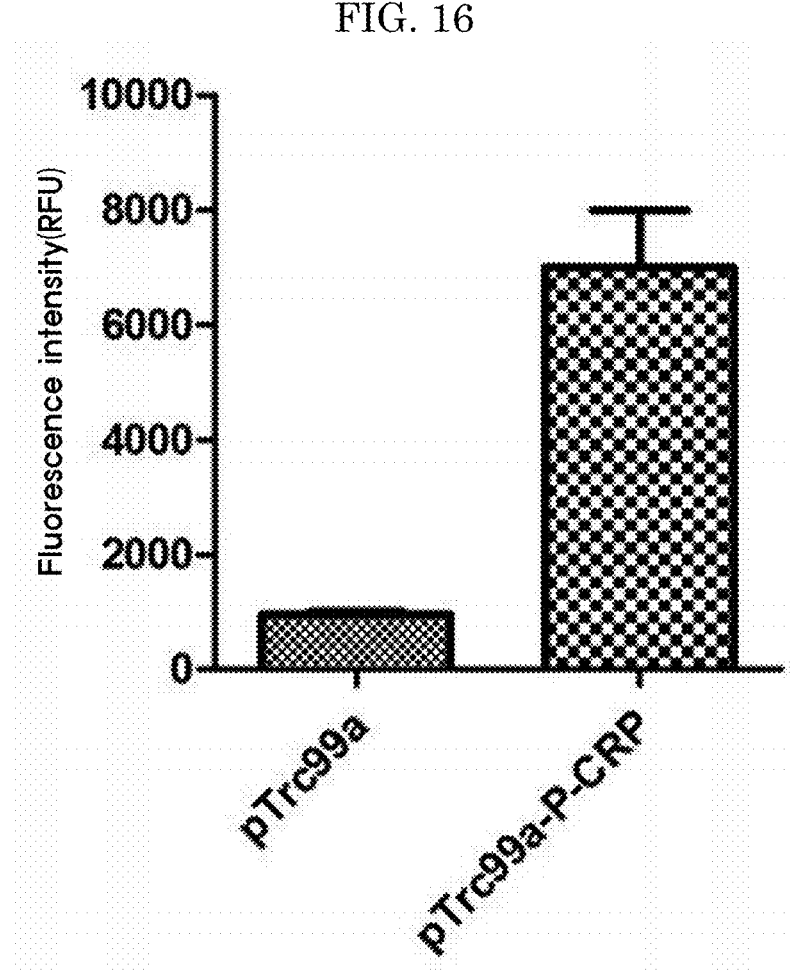
FIG. 16 shows the result of operating the transcriptional induction system in which cGMP is directly used as an inducing agent in the absence of guanylyl cyclase, which corresponds to a variation of the cGMP-dependent orthogonal signal transduction system of the present invention.

According to an inducible expression system, the target gene product is generally expressed in a large amount when there are internal/external inducing agents (chemicals, heat, oxygen, osmotic pressure, or the like) as a signal, and it is widely used in various fields. The most commonly used inducible system is a system in which IPTG is used as an inducing agent. However, being a chemically synthesized inducing agent, it is toxic to cells and, by producing an excess amount of proteins within a short time, a metabolic burden is stressful to the host, and thus it may work as a growth-inhibiting factor. Further, as the inducing agent is expensive, it is not suitable for production of industrial enzymes and bulky chemicals. As such, an inducible expression system using non-chemical inducing agents is preferred and they are required not to be metabolized in a cell or not to disturb other systems. In this regard, cGMP of the present invention is a kind of natural compound satisfying above requirements, and it has not only an excellent property of having no side effects in a living body and also little side reactions that are caused by residual toxicity, as it can be metabolized in a human body. Therefore, a determination was made to see whether or not cGMP can be directly used as a transcription inducer in addition to an orthogonal signal transduction system. To do so, guanylyl cyclase which converts GTP to cGMP molecule was removed, and cGMP was added as an inducing agent to a medium and the level of gene expression was determined. Specific experimental procedures are as follows.

pTrc99a-Cyc-P-CRP plasmid was treated with restriction enzymes BamHI and HindIII to remove the polynucleotide encoding the guanylyl cyclase and according to treatment with a Klenow fragment, self-ligation was induced to complete pTrc99a-P-CRP construct. Among the constructs (pTrc99a-P-CRP, pPRO (0896-GFPuv)3) which has been completed in the same manner as Example 5 above, pPRO (0896-GFPuv)3 was first used for transformation to produce a recombinant strain, and then other plasmids were introduced so that a recombinant having two vectors was produced. As a control group, a strain having empty vector pTrc99a was used. In order to confirm induced expression of a reporter by cGMP in the obtained strain, a transformed single colony of E. coli was pre-cultured in a LB medium containing ampicillin (50 µg/ml) and kanamycin (50 µg/ml) at conditions of 37° C. and 200 rpm. After inoculation to have 1% concentration of the original culture (15 ml), when the absorbance ($OD_{600}$) of the culture reaches 0.5, cGMP dissolved in 0.1% DMSO was added to 500 µM and expression of the green fluorescent protein was induced for 6 hours. The cell culture was sampled every two hours and the fluorescence was measured in the same manner as the above example. As a result, there was indeed expression of the green fluorescent protein, and thus it was confirmed that the gene expression induction can be achieved by directly using cGMP as an inducing agent (FIG. 16).

Example 7. cGMP-Dependent Signal Transduction System Incorporated to Two-Hybrid System The two-hybrid is broadly used in every field of biological studies for determining an interaction between proteins. A typical system of a two-hybrid system which has been first developed in yeast takes advantage of the property of GAL4p protein of Saccharomyces cerevisiae. According to this system, a protein as a subject to study (i.e., bait) is attached to the DNA-binding domain of GAL4p protein to yield a hybrid protein, and the transcription activation domain of GAL4p is attached to a protein which binds to the hybrid protein (i.e., prey) to yield a hybrid protein, and they are simultaneously expressed in yeast. When there is an interacting property between the bait and prey, the two hybrid proteins bind to each other and act like a functional GAL4 protein, i.e., a transcription factor which binds to DNA to induce transcription, and mediates expression of a gene (i.e., reporter) which is located behind the GAL4p binding site (transcription regulatory sequence). As a modification of the two-hybrid technique, a method of searching proteins which interact with each other based on an enzyme activity instead of using transcription factors in dissected form has been also developed. This system is based on a principle that, when a protein having an enzyme activity like beta-lactamase is subjected to domain-dissection and a bait and a prey are fused to each of them followed by expression, and if there is an interaction between fused proteins, the original enzyme functions are recovered so that the activities are shown. A system with dissected transcriptional factors has a disadvantage that there is a time gap as the expression of the reporter needs to be determined as a product of transcription induction and the selection procedure has to be made for all clones. However, in case of a beta-lactamase dissected system, the level of enzyme activity is proportional to the survival ratio and cell growth rate on a medium containing antibiotics, and thus it is advantageous in that the selection processes are very convenient.

In the present example, a method for searching interacting proteins by dissecting guanylyl cyclase using a new two-hybrid system having all the advantages of the aforementioned two methods was developed. According to this new method, when there is an interaction between a bait and a prey that are fused to a dissected domain, domain binding occurs to exhibit the activity, and according to binding of cGMP as an activation product to a receptor, expression of a reporter is induced. The method of the present example has the same signal amplification principle as Example 4 even when the interacting proteins are present in a small amount or have a weak binding property. As such, it can be used as a very effective system for detecting protein interaction. Further, as having an orthogonal signal transduction property, it is a system which is operable in an environment with no interference and has extremely low detection limit, i.e., a system with high sensitivity.

Figure 17:
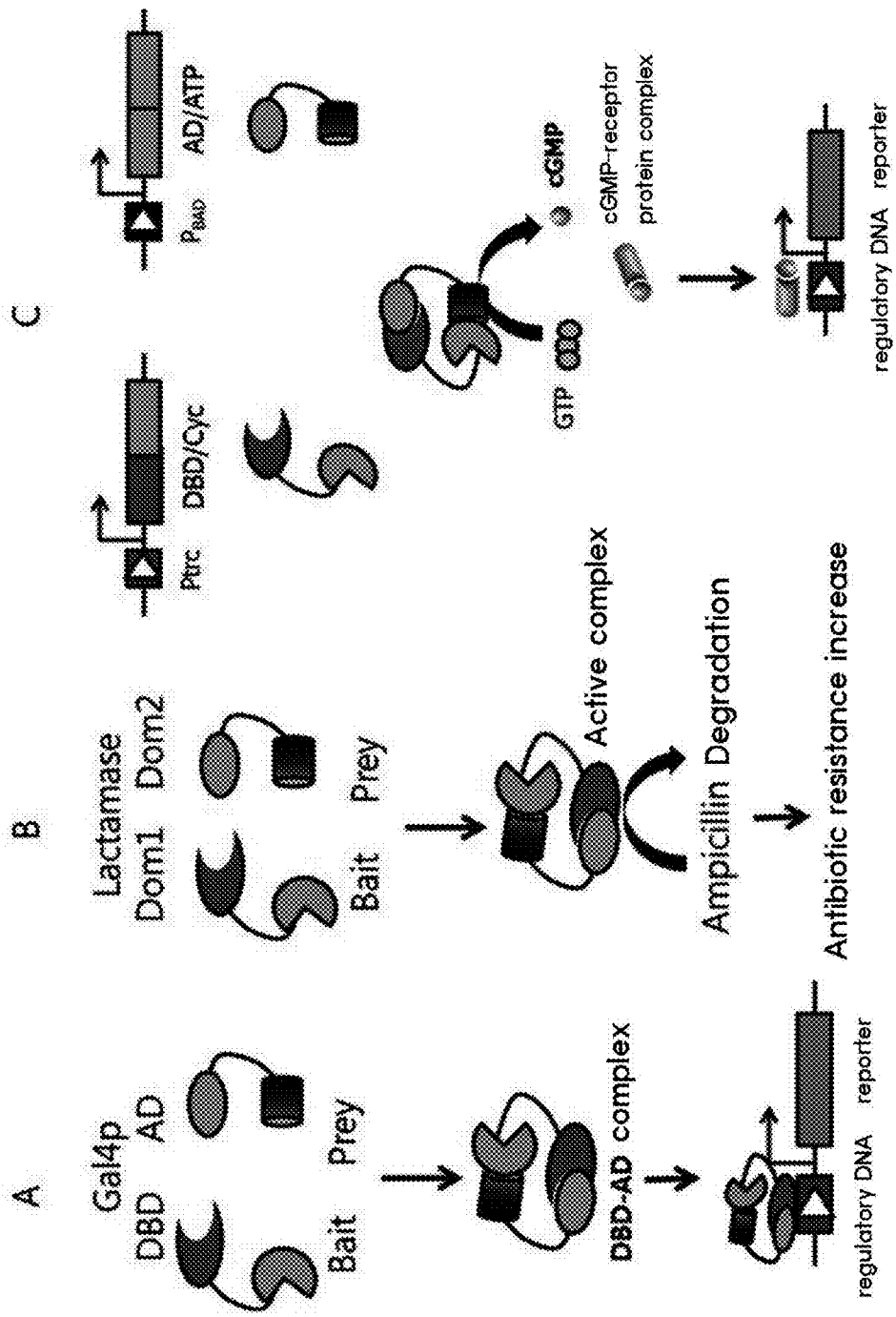
FIG. 17 is a schematic diagram illustrating a principle of a new two-hybrid system in which the guanylyl cyclase as a constitutional element of the cGMP-dependent orthogonal signal transduction system of the present invention is dissected and fused with other protein so as to induce transcription by interaction with the fused protein. A and B represent the operational principle of a two-hybrid system of a related art, and C represents the operational principle of a new orthogonal signal amplifying two-hybrid system in which the signal amplifying effect of the product of the present invention is incorporated.

For achieving the two-hybrid system having protein interactions based on the aforementioned principle, yeast transcriptional factors of which protein-protein interactions have been already confirmed were used as a model for validation of new system. The present example corresponds to a prototype system for confirming the operation, and for an actual process of application, proteins for confirming an interaction are fused to dissected guanylyl cyclase. According to the aforementioned purpose, as a new method for probing a protein-protein interaction of the present example, the cGMP-dependent transcription induction system was designed as follows. Guanylyl cyclase N-terminal domain fused to DNA-binding domain (DBD) of GAL4p protein and guanylyl cyclase C-terminal domain fused to transcription activation domain (AD) of GAL4p were simultaneously expressed in the same host. When there is an interaction between those two fused proteins (i.e., interaction between dissected GAL4p), the domains consisting of guanylyl cyclase are brought into contact to exhibit the activity. As a result, cGMP production is increased to induce the expression of a reporter gene (FIG. 17). Because an orthogonal factor not found in host is used in this system, it is expected that there is no false-positive reaction shown in a two-hybrid system of a related art so that the activity is shown only according to the protein-protein binding in the present invention. An example was carried out as described below.

Figure 18:
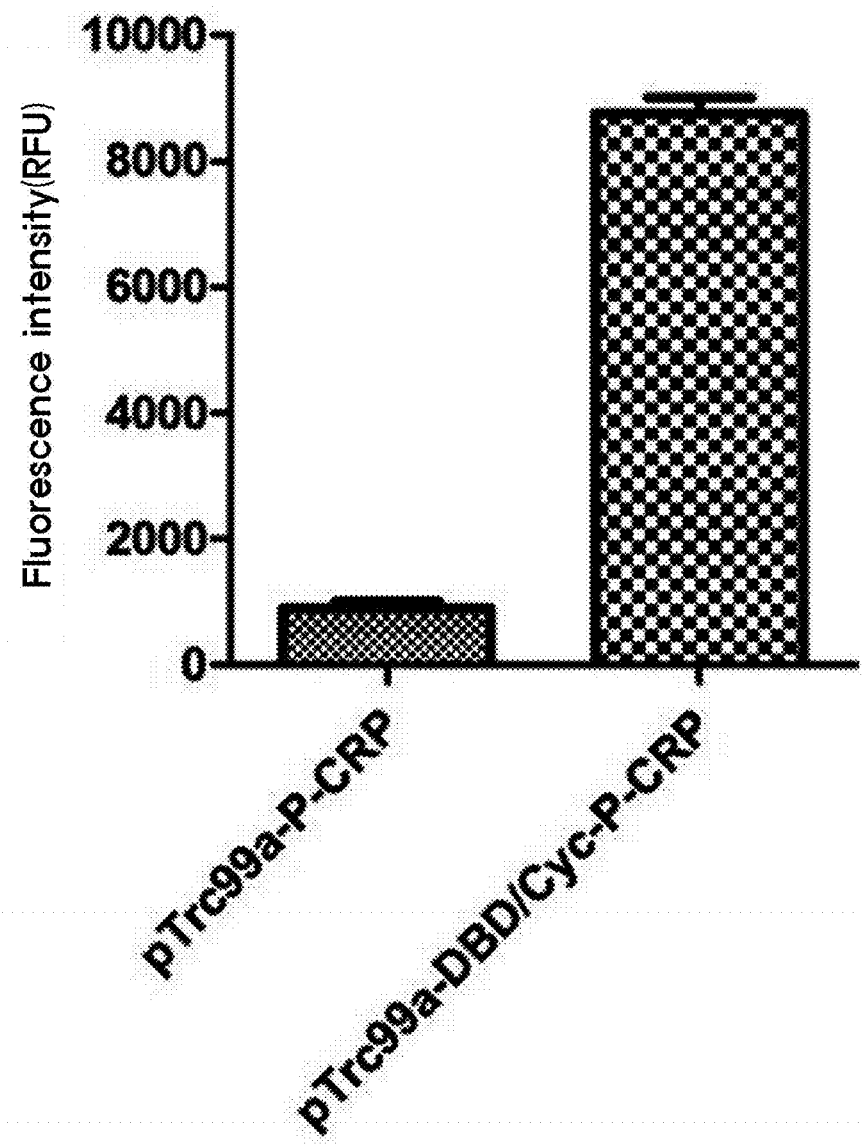
FIG. 18 shows the product according to operation of a new orthogonal signal amplifying two-hybrid system of the present invention, in which a clear difference in signal allowing sensitive and accurate operation by having no interference is shown.

Each of the DNA-binding domain and the transcription activation domain of GAL4p protein was fused to a remaining part containing the catalytic domain (amino acids 14-197) and the ATP hydrolysis domain (amino acids 221-595) of guanylyl cyclase to yield DBD/Cyc and AD/ATP, which were then allowed to express under the control of IPTG-inducible promoter and arabinose-inducible promoter. Plasmids pTrc99a-DBD/Cyc-P-CRP, pBAD-AD/ATP and pPRO0896-GFPuv were used for co-transformation of E. coli. As a control group, cells containing pTrc99a-P-CRP from which DBD/Cyc proteins are removed, pBAD-AD/ATP, and pPRO0896-GFPuv vector were used. After adding 0.1 mM IPTG and 0.0002% arabinose, the green fluorescent protein was measured at different time points. As a result, in case of the cells in which DBD/Cyc and AD/ATP proteins are expressed, the GFP level has dramatically increased in accordance with time. On the other hand, only the fluorescence at basal level was observed from the control group (FIG. 18). This is the result based on the cGMP producing-activity of guanylyl cyclase as caused by an interaction between the DNA-binding domain and transcription activation domain of GAL4p protein. Further, due to the orthogonal characteristics, the interference by interaction with other unspecific proteins is very low, and thus the sensitivity was found to be very high. Thus, it is expected that proteins interacting with a specific protein can be screened with high accuracy and high sensitivity by using this system.

The invention claimed is:

1. A recombinant vector, comprising one or more plasmids,
wherein said one or more plasmids has a gene encoding a guanylyl cyclase, a gene encoding cGMP receptor protein, and a regulatory nucleotide sequence to which cGMP receptor protein binds, and each plasmid has at least one of the gene encoding the guanylyl cyclase, the gene encoding cGMP receptor protein, and the regulatory nucleotide sequence;
the gene encoding the guanylyl cyclase, the gene encoding cGMP receptor protein, and the regulatory nucleotide sequence are derived from a microorganism; and
the regulatory nucleotide sequence consists of the nucleotide sequence of SEQ ID NO: 4 or 5.

2. The recombinant vector according to claim 1, characterized in that the gene encoding a guanylyl cyclase consists of the nucleotide sequence of SEQ ID NO: 1.

3. A recombinant vector having a gene encoding cGMP receptor protein and a regulatory nucleotide sequence to which cGMP receptor protein binds, wherein the gene and the regulatory nucleotide sequence are derived from a microorganism, and the regulatory nucleotide sequence consists of the nucleotide sequence of SEQ ID NO: 4 or 5.

4. The recombinant vector according to claim 1, characterized in that the gene encoding cGMP receptor protein consists of the nucleotide sequence of SEQ ID NO: 3.

5. The recombinant vector of claim 1, wherein a foreign gene is inserted to the downstream of the regulatory nucleotide sequence.

6. A host cell, in culture, transformed with the recombinant vector of claim 5.

7. A method for independent expression of a foreign gene without interfering with a biological circuit of a host cell, the method comprising:
transforming a host cell with the recombinant vector of claim 5, wherein the foreign gene is operably linked to the recombinant vector; and
expressing the foreign gene.

8. The method according to claim 7, characterized in that the host cell is *Escherichia coli*.

9. The recombinant vector according to claim 3, characterized in that the gene encoding cGMP receptor protein consists of the nucleotide sequence of SEQ ID NO: 3.

10. The recombinant vector of claim 3, wherein a foreign gene is inserted to the downstream of the regulatory nucleotide sequence.

11. A host cell transformed with the recombinant vector of claim 5, wherein the host cell is selected from the group consisting of *Escherichia coli, Bacillus* sp., *Salmonella typhimurium, Serratia marcescens* and *Pseudomonas* sp.

12. The recombinant vector of claim 1, wherein the regulatory nucleotide sequence consists of SEQ ID NO: 4.

13. The recombinant vector of claim 1, wherein the regulatory nucleotide sequence consists of SEQ ID NO: 5.

14. The recombinant vector of claim 3, wherein the regulatory nucleotide sequence consists of SEQ ID NO: 4.

15. The recombinant vector of claim 3, wherein the regulatory nucleotide sequence consists of SEQ ID NO: 5.

* * * * *

SEQUENCE LISTING

<160> NUMBER OF SEQ ID NOS: 33

<210> SEQ ID NO 1
<211> LENGTH: 3051
<212> TYPE: DNA
<213> ORGANISM: Rhodospirillum centenum

<400> SEQUENCE: 1

```
atggcgacga gcggaagcac agcgcgcccc ggggcggggg cggggccgc gccggcagga      60
atgaccggcg gggaagccgc cgtgcgctcc gaccggcgca tggccacggt gctgttcgcc     120
gacatcgtgg gctccacccg tatggtcgcc gccgccgacc ccgaggatgc gcaggagcgg    180
ctggaccggg tgctgcgcac cctgtcggcc catgtggaac gctacggcgg gaccgtctgc    240
cagaccctgg gcgacggtat cctggccgtg ttcggcgccc ccaacagcct ggaagatcac    300
gcggtccgcg cctgcttcgc ggccgacgcc atcgtgcggg aggcgcgcag cggcatgcgc    360
gatgccgatc cggtggctgt gcgcgtcggg ctcagttcgg gcgagattct ctgggattcc    420
ggcgcgctca accggcagga ccgtgccccc gcggtgggcc gcacggtgca tctggccgca    480
aaactgcaac agacggcacc ggaaaacggc gtgcgactgt cggagccgac ggccgtcgcc    540
gcgcaggact gggcggaact ggccctggtc ggccgcttcg ccgtcctgcc gaaggatgaa    600
gtcggcgtct tcactcttct ggccatgcgc caccgccgcc gccgggcgga cgacgacccg    660
cccctgttcg gccgtgacga cgtgctcggt gagctgcagg ccgctgtcgc ccgggcgctc    720
gactgtcagg gcggggcctg cctgctggcc gcgccggcgg gcctgggcaa gtcccggctg    780
gccgaagccg tctccgcctt cgcctggcgg gtcggtgccc gtgtcgtcga ctggcggatg    840
cacgcgatgc agcccgtcgg cgtggccgac ccgctgcacg acctggtcac ggccctgctc    900
gacggcgacc tgccggagac gcgggcaccg ctgctccgcc tgatcgaagg gcacggtgcg    960
cgcaaggtgg cggccgaggc cctggccgac ctgctgctgc ccgcggaaga gcgctgcggc   1020
acggcgcagg gggaggatct gctggtcctg gccgccgaag ccgtgggcga tctggtccgg   1080
gccgcggccc ggcggacacc gctgctgctg ctggcggagg acctgcactg ggccggcagc   1140
agtgccgccc ccgtgctgga ccgggtggtg ccgctggtgg gggcgctgcc gctgttcctg   1200
ctcggcaccg cccgggaggt gccgtcctgg ctgcccgacg gggtgcgggt cgtggaactg   1260
gcgccgctgc ccgacgatgc cgcggcagaa ctgaccgccg cgctggtcgg ctcgcacccc   1320
gccctggacg aattgcgcgc ctcgctggtg cggcggaccc agggcaatcc cttcttcctg   1380
caggaatgcg tccgcggcat ggtcgtcagc ggccggctga ccggcattcc cggcgactac   1440
cggccggccg ggctgggcga cgaccggctg ccggagacgg tgcaggcgct gctcgcggcc   1500
cgcatcgaca ccctgcccga acggcaccgc accgtgctgc tggccgcttc cgtcgccggc   1560
gccaccttcg acgccgccct gctggcggca ctcgtgggtt gcggccggac cgccctggtg   1620
gagatcctga cggcgctggc cgacgcggac ttcctggaca cacccgcct gctgccgcgg   1680
ctcgaatact ccttccgcca tgcgctgctg catgaggcgg cctatgccac cctgacccgc   1740
cgcgaccgcc gggcgacgca cgaccgcctg gtcgcgctgc tggaatcacc ggacttcgcc   1800
gatctggcgg ggcgcaaggc ggcgatcgcc cgccacgctt accggagcga ggcctgggcc   1860
```

```
aaggcggcgg aggccggcgg ggaagcgggg ctggaggcgt ccagctttc gctcacctcc     1920 gaagcggtcg atctcctcgg caaggccgtg gacgcgcacg accggctggg cggggcaggg     1980
aacgacccgg cccgtgcctt cgacctgcgt ctgatgctgg cccgcgccac catgccgctg     2040
ggggtggagg gtcacgggcc ggacgtgctg accgggcca tcgacatcgc gcgggcgctg      2100
ggcgatcccg accgggaatg cgccgcctgg ctgctgcgct ccgccttcga ctgggcctat     2160
ggcagcctgc gggacgccgt aacgtcggcc ggacacgcgg tcgaagcctc acgccgcc      2220 gaaggcggtg gcgacccgca tttcgaggtc gaactgcatc acggcaacat cctgctggaa     2280
acgggcaatg tccgtgcggc cctgccgatc ctgcgacatg ccgctgcgat ggccgcgcag     2340
aacgggcagc gtcagggccg ctactgggcg ttggacagcc acatgatgct ggacctccgt     2400
ctggcccgcg gctgatcga gatcggcgag atcgacgccg cccgccgcca cctgccgcg      2460 gccgaggaac acgccgccga agcccgttc cccttcaccc gcatcttctg ctggaccttc     2520
attgccgagg atcacctgct cacgggaggc tggaagctgg cggcgagcta tgccgggcgc     2580
gccctcctgc tcatggagca gacggggtcg cgcatccatt acgggcttgc cacggcactt     2640
gccggactgg tgacggtcac gctcgacggt tcggaggagg gcgtgcgcca gatcgacaag     2700
gggctggcgc aggtgcgcca cgccggacg gcagcgcacg aggcacacat tcttctgctg      2760
cgtgcccagg ccatgggccg gctgggaaac cacttcgagg cgttgcggga tgccgatgcc     2820
gcgctggcgc tggcggagcg gcggcaccag ggcctcgtgg ccgtgcgggc cggcctggaa     2880
tccgcccgcc atgccggcca gctgggcgat gcccgccgct cgcaggagat gctggcccag     2940
gcccgcacct gggcttcctc cctgggtcta tcgacgctgc tgggccagtg cgacgggctg     3000
catgcccgga tcggatcggg cttcgccacg ctcccggctg ccggccgcta g              3051
```

<210> SEQ ID NO 2
<211> LENGTH: 1016
<212> TYPE: PRT
<213> ORGANISM: Rhodospirillum centenum

<400> SEQUENCE: 2

```
Met Ala Thr Ser Gly Ser Thr Ala Arg Pro Gly Ala Gly Ala Gly Ala
1               5                   10                  15

Ala Pro Ala Gly Met Thr Gly Gly Glu Ala Ala Val Arg Ser Asp Arg
                20                  25                  30

Arg Met Ala Thr Val Leu Phe Ala Asp Ile Val Gly Ser Thr Arg Met
            35                  40                  45

Val Ala Ala Ala Asp Pro Glu Asp Ala Gln Glu Arg Leu Asp Arg Val
        50                  55                  60

Leu Arg Thr Leu Ser Ala His Val Glu Arg Tyr Gly Gly Thr Val Cys
65                  70                  75                  80

Gln Thr Leu Gly Asp Gly Ile Leu Ala Val Phe Gly Ala Pro Asn Ser
                85                  90                  95

Leu Glu Asp His Ala Val Arg Ala Cys Phe Ala Ala Asp Ala Ile Val
                100                 105                 110

Arg Glu Ala Arg Ser Gly Met Arg Asp Ala Asp Pro Val Ala Val Arg
            115                 120                 125

Val Gly Leu Ser Ser Gly Glu Ile Leu Trp Asp Ser Gly Ala Leu Asn
        130                 135                 140

Arg Gln Asp Arg Ala Pro Ala Val Gly Arg Thr Val His Leu Ala Ala
145                 150                 155                 160

Lys Leu Gln Gln Thr Ala Pro Glu Asn Gly Val Arg Leu Ser Glu Pro
```

-continued

```
                165                 170                 175
Thr Ala Val Ala Ala Gln Asp Trp Ala Glu Leu Ala Leu Val Gly Arg
            180                 185                 190
Phe Ala Val Leu Pro Lys Asp Glu Val Gly Val Phe Thr Leu Leu Ala
        195                 200                 205
Met Arg His Arg Arg Arg Ala Asp Asp Pro Pro Leu Phe Gly
    210                 215                 220
Arg Asp Asp Val Leu Gly Glu Leu Gln Ala Ala Val Ala Arg Ala Leu
225                 230                 235                 240
Asp Cys Gln Gly Gly Ala Cys Leu Leu Ala Pro Ala Gly Leu Gly
                245                 250                 255
Lys Ser Arg Leu Ala Glu Ala Val Ser Ala Phe Ala Trp Arg Val Gly
            260                 265                 270
Ala Arg Val Val Asp Trp Arg Met His Ala Met Gln Pro Val Gly Val
        275                 280                 285
Ala Asp Pro Leu His Asp Leu Val Thr Ala Leu Leu Asp Gly Asp Leu
    290                 295                 300
Pro Glu Thr Arg Ala Pro Leu Leu Arg Leu Ile Glu Gly His Gly Ala
305                 310                 315                 320
Arg Lys Val Ala Ala Glu Ala Leu Ala Asp Leu Leu Pro Ala Glu
                325                 330                 335
Glu Arg Cys Gly Thr Ala Gln Gly Glu Asp Leu Leu Val Leu Ala Ala
            340                 345                 350
Glu Ala Val Gly Asp Leu Val Arg Ala Ala Arg Arg Thr Pro Leu
        355                 360                 365
Leu Leu Leu Ala Glu Asp Leu His Trp Ala Gly Ser Ser Ala Ala Ala
    370                 375                 380
Val Leu Asp Arg Val Val Pro Leu Val Gly Ala Leu Pro Leu Phe Leu
385                 390                 395                 400
Leu Gly Thr Ala Arg Glu Val Pro Ser Trp Leu Pro Asp Gly Val Arg
                405                 410                 415
Val Val Glu Leu Ala Pro Leu Pro Asp Asp Ala Ala Ala Glu Leu Thr
            420                 425                 430
Ala Ala Leu Val Gly Ser His Pro Ala Leu Asp Glu Leu Arg Ala Ser
        435                 440                 445
Leu Val Arg Arg Thr Gln Gly Asn Pro Phe Phe Leu Gln Glu Cys Val
    450                 455                 460
Arg Gly Met Val Val Ser Gly Arg Leu Thr Gly Ile Pro Gly Asp Tyr
465                 470                 475                 480
Arg Pro Ala Gly Leu Gly Asp Asp Arg Leu Pro Glu Thr Val Gln Ala
                485                 490                 495
Leu Leu Ala Ala Arg Ile Asp Thr Leu Pro Glu Arg His Arg Thr Val
            500                 505                 510
Leu Leu Ala Ala Ser Val Ala Gly Ala Thr Phe Asp Ala Ala Leu Leu
        515                 520                 525
Ala Ala Leu Val Gly Cys Gly Arg Thr Ala Leu Val Glu Ile Leu Thr
    530                 535                 540
Ala Leu Ala Asp Ala Asp Phe Leu Asp Asn Thr Arg Leu Leu Pro Arg
545                 550                 555                 560
Leu Glu Tyr Ser Phe Arg His Ala Leu Leu His Glu Ala Ala Tyr Ala
                565                 570                 575
Thr Leu Thr Arg Arg Asp Arg Arg Ala Thr His Asp Arg Leu Val Ala
            580                 585                 590
```

-continued

```
Leu Leu Glu Ser Pro Asp Phe Ala Asp Leu Ala Gly Arg Lys Ala Ala
        595                 600                 605

Ile Ala Arg His Ala Tyr Arg Ser Glu Ala Trp Ala Lys Ala Ala Glu
    610                 615                 620

Ala Gly Gly Glu Ala Gly Leu Glu Ala Phe Gln Leu Ser Leu Thr Ser
625                 630                 635                 640

Glu Ala Val Asp Leu Leu Gly Lys Ala Val Asp Ala His Asp Arg Leu
                645                 650                 655

Gly Gly Ala Gly Asn Asp Pro Ala Arg Ala Phe Asp Leu Arg Leu Met
                660                 665                 670

Leu Ala Arg Ala Thr Met Pro Leu Gly Val Gly His Gly Pro Asp
    675                 680                 685

Val Leu Asp Arg Ala Ile Asp Ile Ala Arg Ala Leu Gly Asp Pro Asp
    690                 695                 700

Arg Glu Cys Ala Ala Trp Leu Leu Arg Ser Ala Phe Asp Trp Ala Tyr
705                 710                 715                 720

Gly Ser Leu Arg Asp Ala Val Thr Ser Ala Gly His Ala Val Glu Ala
                725                 730                 735

Ser Arg Ala Ala Glu Gly Gly Asp Pro His Phe Glu Val Glu Leu
                740                 745                 750

His His Gly Asn Ile Leu Leu Glu Thr Gly Asn Val Arg Ala Ala Leu
                755                 760                 765

Pro Ile Leu Arg His Ala Ala Met Ala Ala Gln Asn Gly Gln Arg
            770                 775                 780

Gln Gly Arg Tyr Trp Ala Leu Asp Ser His Met Met Leu Asp Leu Arg
785                 790                 795                 800

Leu Ala Arg Gly Leu Ile Glu Ile Gly Glu Ile Asp Ala Ala Arg Arg
                805                 810                 815

His Leu Ala Ala Ala Glu Glu His Ala Ala Glu Ser Pro Phe Pro Phe
                820                 825                 830

Thr Arg Ile Phe Cys Trp Thr Phe Ile Ala Glu Asp His Leu Leu Thr
        835                 840                 845

Gly Gly Trp Lys Leu Ala Ala Ser Tyr Ala Gly Arg Ala Leu Leu Leu
    850                 855                 860

Met Glu Gln Thr Gly Ser Arg Ile His Tyr Gly Leu Ala Thr Ala Leu
865                 870                 875                 880

Ala Gly Leu Val Thr Val Thr Leu Asp Gly Ser Glu Glu Gly Val Arg
                885                 890                 895

Gln Ile Asp Lys Gly Leu Ala Gln Val Arg Gln Arg Thr Ala Ala
                900                 905                 910

His Glu Ala His Ile Leu Leu Leu Arg Ala Gln Ala Met Gly Arg Leu
            915                 920                 925

Gly Asn His Phe Glu Ala Leu Arg Asp Ala Asp Ala Ala Leu Ala Leu
    930                 935                 940

Ala Glu Arg Arg His Gln Gly Leu Val Ala Val Arg Ala Gly Leu Glu
945                 950                 955                 960

Ser Ala Arg His Ala Gly Gln Leu Gly Asp Ala Arg Arg Ser Gln Glu
                965                 970                 975

Met Leu Ala Gln Ala Arg Thr Trp Ala Ser Ser Leu Gly Leu Ser Thr
            980                 985                 990

Leu Leu Gly Gln Cys Asp Gly Leu  His Ala Arg Ile Gly  Ser Gly Phe
        995                 1000                 1005
```

Ala Thr Leu Pro Ala Ala Gly Arg
    1010                1015

<210> SEQ ID NO 3
<211> LENGTH: 708
<212> TYPE: DNA
<213> ORGANISM: Rhodospirillum centenum

<400> SEQUENCE: 3

| | | | | | |
|---|---|---|---|---|---|
| gtgacgcccg | tgcccagcga | cacaaagcgc | atcgacatcg | ccgtgctccg | gcgcaaccga | 60 |
| ctgttcggca | tcctggatgc | tgccgagatg | gaagcggtgc | tggccttcgc | ccaggtccgc | 120 |
| cgcttcgccc | cggacgagcg | catcttcacc | aagggcgatc | cgggcgactg | cctctacgcc | 180 |
| atcctgcgcg | gccgggttgc | cgtccacacg | gaatcggagg | acgccaaggt | gatgctgctg | 240 |
| aacacgctcg | ccgccggcga | ggtgttcgga | gagatcgcca | tgcttgacgg | cggcgagcgc | 300 |
| acggccaccg | tgacggccgc | ggaaccggcg | gacctgctgc | gcatcgaccg | gcgggacttc | 360 |
| ctgcccttcc | tggaggcgcg | gccgaacctc | tgcatccggc | tgatgacggt | gctgtgcgag | 420 |
| cgcctgcgct | ggaccagcgc | catcatcgag | gacacggtct | tcctcaatgt | cccccggcgg | 480 |
| ctggccaagc | gcatcctgat | gctggcgcag | agtgaaggcc | ggcagacgcc | cgacggcatc | 540 |
| cgtatcgcca | ccttcgtctc | ccaggatgcc | ctggcgaaga | tgctgggcgt | atcgcgggag | 600 |
| atcgtgaaca | agaccctgaa | gagtttccag | gccgacggcg | ccatcgccta | tcgcagcggc | 660 |
| tacctgatcg | tccacgacac | ggcctatctg | gagaagctcg | ccggctga | | 708 |

<210> SEQ ID NO 4
<211> LENGTH: 342
<212> TYPE: DNA
<213> ORGANISM: Rhodospirillum centenum

<400> SEQUENCE: 4

| | | | | | |
|---|---|---|---|---|---|
| aggcgacagg | ctcacggatg | cgggctcacg | gcgacggttt | catgcagggc | gcgcgccgtg | 60 |
| gcgggccgat | cctgcgcggc | gcagcttaac | aaatccttcc | ccccggtaaa | ccctgcgggt | 120 |
| tgccccggcc | gggtcacggt | tttccaactc | ttaaccctat | gggtggagta | tgataggaaa | 180 |
| agatagattc | aattttatgc | attccgcgtc | atgccgccgg | ccggaccggg | caccgggatg | 240 |
| catgaaggtg | accggcaggg | tcggtatcca | ggcacggttc | ttgcttgcca | gtgaggcggg | 300 |
| aaccaagtcc | ggtgcaagcc | aagtcgggca | gggaagggtg | tc | | 342 |

<210> SEQ ID NO 5
<211> LENGTH: 212
<212> TYPE: DNA
<213> ORGANISM: Rhodospirillum centenum

<400> SEQUENCE: 5

| | | | | | |
|---|---|---|---|---|---|
| tggctttcct | ccttttcgg | gcagccggac | gggtgccctc | gggcgccaca | acagacgacg | 60 |
| cgacgcgata | tcggcgtggc | cgccgggttt | tcacacccct | tttccagcga | catccgcgcc | 120 |
| cgcggcaggg | gcctgatcct | cgaccgctgc | gggacggccc | cgcagcggca | gcccttgcgc | 180 |
| ggggggaggc | cggaagccat | agtcccggac | cc | | | 212 |

<210> SEQ ID NO 6
<211> LENGTH: 267
<212> TYPE: DNA
<213> ORGANISM: Rhodospirillum centenum

<400> SEQUENCE: 6

-continued

```
cgcttccccc gtggatgcgc ttcccctgtg gatgcgcgga gcggcacgcc ggcccccgcc    60
gcccgggaaa cggtcgcggt tcgggccagg ccgcgcctgc cggtgagggg cgcactctag   120
cggggatggc cggcccggtc cctacgcgat ggggcgtagg acgaaggacc gggtcgcccc   180
ggccgaaagc gatgggtccc ggccggacgg gtccgcgcgg acggggccgg cgcggatggg   240
gccggcgcgg atggggccgg cggcggt                                       267
```

<210> SEQ ID NO 7
<211> LENGTH: 220
<212> TYPE: DNA
<213> ORGANISM: Rhodospirillum centenum

<400> SEQUENCE: 7

```
aggctcggct cgctggaacg ggcggccgca gcatagtcca gagggccggc cgttggacat    60
aacgccgatg gatgataccg ccccccgacg atggatgtaa cagcatccgg gtcctatgac   120
ctgcccgcgg catcagaccg ggccgctctg aacgggccgg tcagccccccc ggccggtcag   180 gccgggccgg tcagcccccg gccggtcagg ccgggccggt                         220
```

<210> SEQ ID NO 8
<211> LENGTH: 29
<212> TYPE: DNA
<213> ORGANISM: Artificial Sequence
<220> FEATURE:
<223> OTHER INFORMATION: Primer

<400> SEQUENCE: 8

```
ctgggatcca tggcgacgag cggaagcac                                      29
```

<210> SEQ ID NO 9
<211> LENGTH: 30
<212> TYPE: DNA
<213> ORGANISM: Artificial Sequence
<220> FEATURE:
<223> OTHER INFORMATION: Primer

<400> SEQUENCE: 9

```
cagtcgacga cacgggcacc gacccgccag                                     30
```

<210> SEQ ID NO 10
<211> LENGTH: 30
<212> TYPE: DNA
<213> ORGANISM: Artificial Sequence
<220> FEATURE:
<223> OTHER INFORMATION: Primer

<400> SEQUENCE: 10

```
tcgtcgactg gcggatgcac gcgatgcagc                                     30
```

<210> SEQ ID NO 11
<211> LENGTH: 35
<212> TYPE: DNA
<213> ORGANISM: Artificial Sequence
<220> FEATURE:
<223> OTHER INFORMATION: Primer

<400> SEQUENCE: 11

```
atgggcccaa gcttctagcg gccggcagcc gggag                               35
```

<210> SEQ ID NO 12
<211> LENGTH: 30
<212> TYPE: DNA
<213> ORGANISM: Artificial Sequence
<220> FEATURE:
<223> OTHER INFORMATION: Primer

<400> SEQUENCE: 12
cggggatcct ctagagaatt cattaaagag                               30

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
cagaagcttt cagccggcga gctt                                    24

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
ataaagctta tagggggatc cgcg                                    24

<210> SEQ ID NO 15
<211> LENGTH: 30
<212> TYPE: DNA
<213> ORGANISM: Artificial Sequence
<220> FEATURE:
<223> OTHER INFORMATION: Primer

<400> SEQUENCE: 15
atgcgatcct ctcattctag aggatccccg                              30

<210> SEQ ID NO 16
<211> LENGTH: 29
<212> TYPE: DNA
<213> ORGANISM: Artificial Sequence
<220> FEATURE:
<223> OTHER INFORMATION: Primer

<400> SEQUENCE: 16
atagtgcaca ggcgacaggc tcacggatg                               29

<210> SEQ ID NO 17
<211> LENGTH: 35
<212> TYPE: DNA
<213> ORGANISM: Artificial Sequence
<220> FEATURE:
<223> OTHER INFORMATION: Primer

<400> SEQUENCE: 17
ttctccttta ctcatgacac ccttccctgc ccgac                        35

<210> SEQ ID NO 18
<211> LENGTH: 35
<212> TYPE: DNA
<213> ORGANISM: Artificial Sequence
<220> FEATURE:
<223> OTHER INFORMATION: Primer

<400> SEQUENCE: 18
ttctccttta ctcattggct ttcctccttt ttcgg                        35

<210> SEQ ID NO 19
<211> LENGTH: 29
<212> TYPE: DNA
<213> ORGANISM: Artificial Sequence
<220> FEATURE:
<223> OTHER INFORMATION: Primer

<400> SEQUENCE: 19
tatgaattcg ggtccgggac tatggcttc                              29

<210> SEQ ID NO 20
<211> LENGTH: 35
<212> TYPE: DNA
<213> ORGANISM: Artificial Sequence
<220> FEATURE:
<223> OTHER INFORMATION: Primer

<400> SEQUENCE: 20
ttctccttta ctcatcgctt ccccgtgga tgcgc                        35

<210> SEQ ID NO 21
<211> LENGTH: 29
<212> TYPE: DNA
<213> ORGANISM: Artificial Sequence
<220> FEATURE:
<223> OTHER INFORMATION: Primer

<400> SEQUENCE: 21
tatgaattca ccgccgccgg ccccatccg                              29

<210> SEQ ID NO 22
<211> LENGTH: 35
<212> TYPE: DNA
<213> ORGANISM: Artificial Sequence
<220> FEATURE:
<223> OTHER INFORMATION: Primer

<400> SEQUENCE: 22
ttctccttta ctcataggct cggctcgctg gaacg                       35

<210> SEQ ID NO 23
<211> LENGTH: 29
<212> TYPE: DNA
<213> ORGANISM: Artificial Sequence
<220> FEATURE:
<223> OTHER INFORMATION: Primer

<400> SEQUENCE: 23
tatgaattca ccggcccggc ctgaccggc                              29

<210> SEQ ID NO 24
<211> LENGTH: 35
<212> TYPE: DNA
<213> ORGANISM: Artificial Sequence
<220> FEATURE:
<223> OTHER INFORMATION: Primer

<400> SEQUENCE: 24
gtcgggcagg gaagggtgtc atgagtaaag gagaa                       35

<210> SEQ ID NO 25
<211> LENGTH: 29
<212> TYPE: DNA
<213> ORGANISM: Artificial Sequence
<220> FEATURE:
<223> OTHER INFORMATION: Primer

<400> SEQUENCE: 25
gcggaattct tatttgtaga gctcatcca                                29

<210> SEQ ID NO 26
<211> LENGTH: 29
<212> TYPE: DNA
<213> ORGANISM: Artificial Sequence
<220> FEATURE:
<223> OTHER INFORMATION: Primer

<400> SEQUENCE: 26
cgggtgcact tatttgtaga gctcatcca                                29

<210> SEQ ID NO 27
<211> LENGTH: 35
<212> TYPE: DNA
<213> ORGANISM: Artificial Sequence
<220> FEATURE:
<223> OTHER INFORMATION: Primer

<400> SEQUENCE: 27
ccgaaaaagg aggaaagcca atgagtaaag gagaa                         35

<210> SEQ ID NO 28
<211> LENGTH: 35
<212> TYPE: DNA
<213> ORGANISM: Artificial Sequence
<220> FEATURE:
<223> OTHER INFORMATION: Primer

<400> SEQUENCE: 28
gcgcatccac gggggaagcg atgagtaaag gagaa                         35

<210> SEQ ID NO 29
<211> LENGTH: 35
<212> TYPE: DNA
<213> ORGANISM: Artificial Sequence
<220> FEATURE:
<223> OTHER INFORMATION: Primer

<400> SEQUENCE: 29
cgttccagcg agccgagcct atgagtaaag gagaa                         35

<210> SEQ ID NO 30
<211> LENGTH: 21
<212> TYPE: DNA
<213> ORGANISM: Artificial Sequence
<220> FEATURE:
<223> OTHER INFORMATION: Primer

<400> SEQUENCE: 30
cgcgtcttgt agttcccgtc a                                        21

<210> SEQ ID NO 31
<211> LENGTH: 23
<212> TYPE: DNA
<213> ORGANISM: Artificial Sequence
<220> FEATURE:
<223> OTHER INFORMATION: Primer

<400> SEQUENCE: 31
tgacaagtgt tggccatgga aca                                      23

<210> SEQ ID NO 32

```
<211> LENGTH: 18
<212> TYPE: DNA
<213> ORGANISM: Artificial Sequence
<220> FEATURE:
<223> OTHER INFORMATION: Primer

<400> SEQUENCE: 32
tgatccggct aacctgaa                                              18

<210> SEQ ID NO 33
<211> LENGTH: 18
<212> TYPE: DNA
<213> ORGANISM: Artificial Sequence
<220> FEATURE:
<223> OTHER INFORMATION: Primer

<400> SEQUENCE: 33
gcggtgatgt gtttacga                                              18
```